(12) United States Patent  (10) Patent No.: US 6,211,240 B1
Zurflüh  (45) Date of Patent: Apr. 3, 2001

(54) O-BENZYL OXIME ETHER DERIVATIVES AND THEIR USE AS PESTICIDES

(75) Inventor: René Zurflüh, Bülach (CH)

(73) Assignee: Novartis Corporation, Summit, NJ (US)

( * ) Notice: Subject to any disclaimer, the term of this patent is extended or adjusted under 35 U.S.C. 154(b) by 0 days.

(21) Appl. No.: 08/739,388

(22) Filed: Oct. 29, 1996

Related U.S. Application Data

(62) Division of application No. 08/374,535, filed as application No. PCT/EP94/01457 on May 6, 1994, now abandoned.

(30) Foreign Application Priority Data

May 18, 1993 (CH) .................................................. 1516/93

(51) Int. Cl.[7] .......................... A01N 43/42; A01N 43/82; A01N 37/34; A01N 37/18

(52) U.S. Cl. ...................... 514/599; 514/238.2; 514/311; 514/357; 514/365; 514/438; 514/466; 514/469; 514/471; 514/529; 544/160; 546/77; 546/175; 546/331; 548/204; 549/441; 549/495

(58) Field of Search ............................... 564/74; 514/599, 514/238.2, 311, 357, 365, 438, 466, 469, 471, 524; 544/160; 546/77, 175, 331; 548/204; 549/495, 441; 558/422

(56) References Cited

U.S. PATENT DOCUMENTS 5,248,687 * 9/1993 Hayase et al. ........................ 514/346
5,387,607 * 2/1995 Brand et al. .......................... 514/513
5,446,067   8/1995 Benoit et al. ......................... 564/256

FOREIGN PATENT DOCUMENTS 370629   5/1990 (EP) .
0398692 11/1990 (EP) .
463488   1/1992 (EP) .
342468   5/1992 (EP) ................................. C07K/7/08
528681   2/1993 (EP) .
359873   9/1993 (EP) ............................... A61K/37/54
0602514  6/1994 (EP) .
WO 91/07164 5/1991 (WO) .............................. A61K/7/32
WO/9213830 8/1992 (WO) .

OTHER PUBLICATIONS

Chemical Abstract JP 5–294948A (Nippon Nohyaku Co).
Chemical Abstract JP 5–201946A (Mitsubishi Kasei).

(List continued on next page.)

Primary Examiner—Peter O'Sullivan
(74) Attorney, Agent, or Firm—William A. Teoli; Edward McC. Roberts; Michael P. Morris

(57) ABSTRACT

Compounds of the formula I

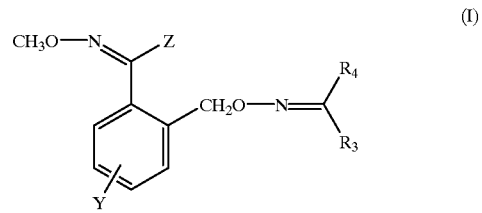

(I)

in which
Y is hydrogen, $C_1$–$C_4$alkyl, $C_1$–$C_4$alkoxy, OH, CN, $NO_2$, $Si(CH_3)_3$, $CF_3$ or halogen,
Z is a group a)

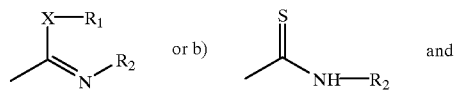

$R_1$ is hydrogen, $C_1$–$C_4$alkyl, $C_2$–$C_4$alkenyl, $C_2$–$C_4$-alkynyl, $C_3$–$C_6$cycloalkyl, phenyl which is unsubstituted or at most trisubstituted by halogen, $C_1$–$C_4$alkyl, $C_1$–$C_4$alkoxy, $C_1$–$C_4$alkylthio, or benzyl which is unsubstituted or at most trisubstituted in the aromatic ring in the same manner; or is cyclopropylmethyl, $C_1$–$C_4$haloalkyl, $C_2$–$C_5$alkoxyalkyl, cyanomethyl, CO—$R_6$, OH, $NH_2$, $C_1$–$C_4$alkylamine or $C_1$–$C_4$alkoxycarbonyl-$C_1$–$C_2$alkyl;
X is oxygen, sulfur or $NR_5$;
$R_2$ is hydrogen, $C_1$–$C_4$alkyl, $C_2$–$C_4$alkenyl, $C_2$–$C_4$alkynyl, $C_3$–$C_6$cycloalkyl, $C(O)R_6$, OH or $C_1$–$C_4$alkoxy, $NH_2$ or $C_1$–$C_4$alkylamine;
$R_5$ is hydrogen, $C_1$–$C_4$alkyl, $C_2$–$C_4$alkenyl or $C_2$–$C_4$alkynyl;
$R_6$ is hydrogen, $C_1$14 $C_4$alkyl, $C_1$–$C_4$haloalkyl, $C_1$–$C_4$alkoxy, $C_3$–$C_6$cycloalkyl, $C_1$–$C_4$alkoxycarbonyl or phenyl which is unsubstituted or at most trisubstituted; and in which $R_3$ and $R_4$ independently of one another are hydrogen, cyano, $C_1$–$C_4$alkyl, halo$C_1$–$C_4$alkyl, $C_2$–$C_4$alkenyl, $C_2$–$C_4$alkynyl, $C_3$–$C_6$cycloalkyl, cyclopropylmethyl, $C_1$–$C_4$alkoxy, $C_2$–$C_5$alkoxyalkyl, $C_2$–$C_4$alkoxycarbonyl, $C_1$–$C_4$alkylthio, $C_2$–$C_5$–alkylthioalkyl; a ring having not more than 15 ring carbon atoms which can be polymembered and is unsubstituted or at most trisubstituted and has 0–3 hetero atoms N, O or S, it being possible for this ring to be bonded via an aliphatic bridge having not more than 4 carbon atoms and/or via either CO, oxygen or sulfur; or
in which $R_3$ and $R_4$ together with the shared carbon atom are a ring or a polymembered ring system having not more than 15 ring carbon atoms which is unsubstituted or at most trisubstituted and has 0–3 hetero atoms N, O or S;
are suitable for controlling and preventing attack by microorganisms of plants. They can be used in the form of commercially available formulated compositions.

15 Claims, No Drawings -

OTHER PUBLICATIONS

Hogan, J.S., et al. "Protocols for Evaluating Efficacy of Postmiking Teat Dips" J. Dairy Sci. 73: 2580–2585 1990.

Jung, D.S. et al. Influence of Fat Emulsifiers on the Efficacy of Nisin in Inhibiting *Listeria monocytogenes* in Fluid Milk, J. Dairy Sci. 75: 387–393 1992.

Cullor J.S., et al. *Disorders of the Organ Systems* pp. 1047–1067 (1965).

Philpot, W.N. "Economics of Mastitis Control" Veterinary Clinics of North America: Large Animal Practice 6, No. 2 pp. 233–245.

Schnell, N. et a., Structural Gene Isolation and Prepeptide Sequence of Gallidermin a New Lanthionine Containing Antibiotic, FEMS Microbiology Letters 58 pp. 263–268 1989.

Fiedler, H.P., et al., Purification of the Hydrophilic Antibiotics Epidermin, Gallidermin and Nikkomycin Z by Preparative Reversed–Phase NPLC, Chromtographia 26 pp. 215–220 1988.

Chem. Abstract, vol. 120, 270454 h (1994).

Chem. Abstract, vol. 119, 264648 n (1993).

* cited by examiner

O-BENZYL OXIME ETHER DERIVATIVES AND THEIR USE AS PESTICIDES

This is a division of application Ser. No. 08/374,535, now abandoned, 35 USC 371 date of Jan. 17, 1995, originally International application PCT/EP 94/01457, filed May 6, 1994.

The present invention relates to compounds of the formula I

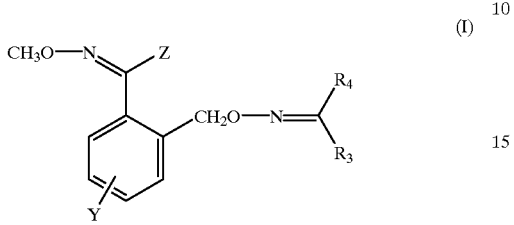

in which
Y is hydrogen, $C_1$–$C_4$alkyl, $C_1$–$C_4$alkoxy, OH, CN, $NO_2$, $Si(CH_3)_3$, $CF_3$ or halogen,
Z is a group a)

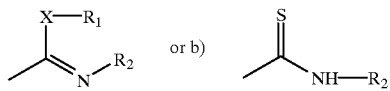

and in which the remaining substituents are defined as follows:

$R_1$ is hydrogen, $C_1$–$C_4$alkyl, $C_2$–$C_4$alkenyl, $C_2$–$C_4$-alkynyl, $C_3$–$C_6$cycloalkyl, phenyl which is unsubstituted or at most trisubstituted by halogen, $C_1$–$C_4$alkyl, $C_1$–$C_4$alkoxy, $C_1$–$C_4$alkylthio, or benzyl which is unsubstituted or at most trisubstituted in the aromatic ring in the same manner or is cyclopropylmethyl, $C_1$–$C_4$haloalkyl, $C_2$–$C_5$alkoxyalkyl, cyanomethyl, CO—$R_6$, OH, $NH_2$, $C_1$–$C_4$alkylamine or $C_1$–$C_4$alkoxycarbonyl-$C_1$–$C_2$alkyl;

X is oxygen, sulfur or $NR_5$;

$R_2$ is hydrogen, $C_1$–$C_4$alkyl, $C_2$–$C_4$alkenyl, $C_2$–$C_4$alkynyl, $C_3$–$C_6$cycloalkyl, $C(O)R_6$, OH $C_1$–$C_4$alkoxy, $NH_2$ or $C_1$–$C_4$alkylamine;

$R_5$ is hydrogen, $C_1$–$C_4$alkyl, $C_2$–$C_4$alkenyl or $C_2$–$C_4$alkynyl;

$R_6$ is hydrogen, $C_1$–$C_4$alkyl, $C_1C_4$haloalkyl, $C_{C_4}$alkoxy, $C_3$–$C_6$cycloalkyl, $C_1$–$C_4$alkoxycarbonyl or phenyl which is unsubstituted or at most trisubstituted;

and in which $R_3$ and $R_4$ independently of one another are hydrogen, cyano, $C_1$–$C_4$alkyl, halo-$C_1$–$C_4$alkyl, $C_2$–$C_4$alkenyl, $C_2$–$C_4$alkynyl, $C_3$–$C_6$cycloalkyl, cyclopropylmethyl, $C_1C_4$alkoxy, $C_2$–$C_5$alkoxyalkyl, $C_1$–$C_4$alkoxycarbonyl, $C_1$–$C_4$alkylthio, $C_2$–$C_5$alkylthioalkyl; a ring having not more than 15 ring carbon atoms which can be polymembered, and is unsubstituted or at most trisubstituted and has 0–3 hetero atoms N, O or S, it being possible for this ring to be bonded via an aliphatic bridge having not more than 4 carbon atoms and/or via either CO, oxygen or sulfur, or
in which $R_3$ and $R_4$ together with the shared carbon atom are a ring or a polymembered ring system having not more than 15 ring carbon atoms which is unsubstituted or at most trisubstituted and has 0–3 hetero atoms N, O or S;

the possible substituents of all these rings mentioned for $R_3$ and $R_4$, either individually or in combination, being selected from amongst $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1C_4$alkoxymethyl, $C_1$–$C_4$alkylcarbonyl, $C_1$–$C_4$alkoxycarbonyl, $C_1$–$C_4$alkoximinomethyl, —$CSNH_2$, —SH, $C_1$–$C_4$alkylthio, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl; phenyl, benzyl, phenoxy, phenylthio, benzyloxy and benzylthio; it being possible for the last-mentioned aromatic substituents to have not more than three further substituents in the phenyl ring which are selected from amongst halogen, $C_1$–$C_4$alkyl, $C_1$–$C_4$alkoxy, $C_1$–$C_4$haloalkyl, $C_1$–$C_4$haloalkoxy, CN and $NO_2$ and it being possible for two of the substituents, of which there are not more than 3, to form, together with the adjacent substituents, an aliphatic bridge which has not more than 5 members and which has 0–2 oxygen atoms and 0–1 carbonyl group and which can be not more than tetrasubstituted by halogen, $C_1$–$C_4$alkyl, $C_1$–$C_4$alkoxy and/or by a single phenyl group.

In a narrower sense of the meaning the invention refers also to the above-mentioned group of compounds of formula I, wherein $R_1$ is hydrogen, $C_1$–$C_4$alkyl, $C_2$–$C_4$alkenyl, $C_2$–$C_4$alkynyl, $C_3$–$C_6$cycloalkyl; or is phenyl which is unsubstituted or at most trisubstituted by halogen, $C_1$–$C_4$alkyl, $C_1$–$C_4$alkoxy, $C_1$–$C_4$alkylthio; or is benzyl which is unsubstituted or at most trisubstituted in the aromatic ring in the same manner, and wherein $R_2$ is hydrogen, $C_1$–$C_4$alkyl, $C_2$–$C_4$alkenyl, $C_2$–$C_4$alkynyl, $C_3$–$C_6$cycloalkyl, C(O)$R_6$, OH or $C_1$–$C_4$alkoxy.

If asymmetric carbon atoms are present in the compounds of the formula I, the compounds occur in optically active form. On account of the presence of the imino double bond on its own, the compounds in any case occur in the [E]- or [Z]-form. Atropisomerism can also occur. The formula I is intended to include all these possible isomeric formulae and also their mixtures, e.g. racemic mixtures and any desired [E/Z]-mixtures.

The compounds according to the invention have fungicidal properties and are suitable as fungicidal active ingredients in crop protection.

If the compounds I have at least one basic centre, they can form acid addition salts. These are formed, for example, with strong inorganic acids, such as mineral acids, for example sulfuric acid, a phosphoric acid or a hydrohalic acid, with strong organic carboxylic acids, such as $C_1$–$C_4$alkanecarboxylic acids which are unsubstituted or substituted, for example by halogen, for example acetic acid, such as saturated or unsaturated dicarboxylic acids, for example oxalic acid, malonic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$–$C_4$alkane- or arylsulfonic acids which are unsubstituted or substituted, for example by halogen, for example methane- or p-toluenesulfonic acid. Due to the close relationship between the compounds I in free form and in the form of their salts, they are, analogously, to be understood as meaning, if appropriate, the relevant salts or the free compounds I.

Unless otherwise defined, the general terms used hereinabove and hereinafter are defined as follows.

Alkyl groups on their own or as structural element of other groups are straight-chain or branched, depending on the number of carbon atoms. $C_1$–$C_4$Alkyl is methyl, ethyl, propyl, isopropyl, butyl, isobutyl, sec-butyl and tert-butyl.

Alkenyl as a group or as structural element of other groups and compounds, such as alkenyloxy, arylalkenyl and heteroarylalkenyl, is either straight-chain, for example ethenyl, propen-1-yl or but-1-en-1-yl, or branched, for example propen-2-yl or but-1-en-2-yl.

Alkynyl as a group or as structural element of other groups and compounds, such as alkynyloxy, is either straight-chain, for example ethynyl, propyn-1-yl or but-1-yn-1-yl, or branched, for example propyn-2-yl or but-1-yn-2-yl.

Cycloalkyl as a group or as structural element of other groups and compounds, such as cycloalkylmethoxy, is, for example, cyclopropyl, cyclobutyl, cyclopentyl or cyclohexyl.

Carbocyclic rings on their own or as structural element of other groups, such as aryl-$C_1$–$C_4$alkyl, aryloxy-$C_1$–$C_4$alkyl, arylthio-$C_1$–$C_4$alkyl, arylcarbonyl and aryl-$C_2$–$C_4$alkenyl groups, have, in particular, 6 to 14 C atoms and are, for example, naphthyl, tetrahydronaphthyl, indanyl, fluorenyl, phenanthryl or in particular phenyl. They can be aromatic, partially hydrogenated or completely saturated. One or two benzene rings may be fused to carbocyclic rings.

Rings having hetero atoms, as a group as such and as structural element of other groups and compounds, such as heteroaryl-$C_1$–$C_4$alkyl, heteroaryloxy-$C_1$–$C_4$alkyl, heteroarylthio-$C_1$–$C_4$alkyl, heteroarylcarbonyl and heteroaryl-$C_2$–$C_4$alkenyl groups, have, in particular, 5 to 14 ring members, of which 1 to 3 members are hetero atoms selected from amongst the group oxygen, sulfur and nitrogen. Examples which may be mentioned are benzimidazolyl, benzocumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, ethylenedioxyphenyl, furyl, imidazolyl, indazolyl, indolyl, isoquinolyl, isothiazolyl, isoxazolyl, methylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4b]pyridyl, pyridyl, pyrimidinyl, pyrrolyl, tetrazolyl, thiadiazolyl, thiazolyl, thienyl, triazinyl and triazolyl.

Preferred heteroaryl radicals $R_3$ and/or $R_4$ are benzofuryl, benzothienyl, quinolyl, quinoxalinyl, dihydrobenzofuryl, ethylenedioxy, furyl, methylenedioxy, pyridyl, pyrimidinyl, pyrrolyl, thiazolyl and thienyl.

One or two benzene rings may be fused to heterocyclic rings.

Halogen is fluorine, chlorine, bromine or iodine. Examples of haloalkyl and haloalkoxy groups are —$CH_2F$, —$CHF_2$, —$CF_3$, —$CH_2Cl$, —$CHCl_2$, —$CHCl_2$, —$CCl_3$, —$CCl_2CCl_3$, —$CH_2Br$, —$CH_2CH_2Br$, —$CHBrCl$, —$OCHF_2$, $OCF_3$, $OCH_2CF_3$, $OCF_2CHF_2$ and $OCF_2CHFCF_3$.

One of the preferred groups of the formula I is formed by those compounds in which Z is the group a) in which X is oxygen and $R_1$ is $C_1$–$C_4$alkyl, while $R_2$ is hydrogen, $C_1$–$C_4$alkyl, OH or $C_1$–$C_4$alkoxy.

Preferred amongst these are those compounds in which $R_1$ is methyl and $R_2$ is hydrogen or methyl.

Another preferred group of the formula I is formed by those compounds in which Z is the group a) in which X is sulfur and $R_1$ is methyl or ethyl, while $R_2$ is hydrogen or $C_1$–$C_4$alkyl.

Another preferred group of the formula I is formed by those compounds in which Z is the group a) in which X is sulfur, $R_1$ is methyl, ethyl, allyl, benzyl, cyclopropylmethyl; $R_2$ is hydrogen, $C_1$–$C_2$alkyl; $R_3$ is methyl, methoxy, methylthio or cyclopropyl; and $R_4$ is phenyl which is mono- or di-substituted in 3- and/or 4-position with one or two substituents selected from the group consisting of halogen, methoxy, trifluoromethyl and trifluoromethoxy.

This group will be designated subgroup ICC.

Preferred compounds within the scope of this group ICC are those, wherein $R_4$ is 3-chlorophenyl, 3-bromophenyl, 4-chlorophenyl, 4-bromophenyl, 3-trifluoromethylphenyl, 3-trifluoromethoxyphenyl, 3-fluoro-4-methoxyphenyl or 3-chloro-4-methoxyphenyl.

This group will be designated subgroup Icc.

Another preferred group of the formula I is formed by those compounds in which Z is the group a) in which X is —$NR_5$—and $R_5$ is hydrogen or $C_1$–$C_4$alkyl, while $R_1$ and $R_2$ independently are hydrogen or $C_1$–$C_4$alkyl.

Preferred compounds amongst the last-mentioned ones are those in which $R_1$, $R_2$ and $R_5$ independently are hydrogen or methyl.

An important group of compounds is formed by those compounds of the formula I in which the substituents are defined as follows:

Y is hydrogen,

Z is a group a) where X is oxygen or group b), $R_1$ is $C_1$–$C_4$alkyl $R_2$ is H, $C_1$–$C_4$alkyl, OH, $C_1$–$C_4$alkoxy $R_3$ is H, $C_1$–$C_4$alkyl, cyclopropyl, $C_1$–$C_2$alkoxy, $C_1$–$C_2$alkylthio, methoxymethyl, cyano, trifluoromethyl, $R_4$ is halophenyl having 1 to 2 halogen atoms, mono-$C_1$–$C_2$alkylphenyl, monohalo-mono-($C_1$–$C_2$alkoxy) phenyl, mono-($C_1$–$C_4$-alkoxy)phenyl, 3-(halo-$C_1$–$C_4$alkyl)phenyl having 1 to 3 halogen atoms, trifluoromethylphenyl which is substituted by fluorine or chlorine, 3-(halo-$C_1$–$C_4$alkoxy)phenyl having 1 to 6 halogen atoms (in particular fluorine), 3-($C_2$–$C_4$alkenyloxy)phenyl, 3-($C_2$–$C_4$alkynyloxy) phenyl, 3-($C_3$-$C_6$cycloalkylmethoxy)phenyl, 3-(cyano-$C_1$–$C_3$alkoxy)phenyl, bis(trifluoromethyl)phenyl, tolyl which is substituted by fluorine or chlorine, monocyanophenyl, trifluoromethylphenyl which is substituted by methylthio, or 3-(trimethylsilyl)phenyl, methoxynitrophenyl, 3- or 4-phenoxyphenyl; 3-(methylsulfinylmethyl)- or 3-(methylsulfonylmethyl) phenyl which are unsubstituted or substituted by methoxy; or 3-trifluoromethyl, 4-chlorobenzyl, 3-(trifluoromethyl)phenoxymethyl, 3-trifluoromethylbenzoyl, 2-naphthyl, phenyl which is substituted in the 3- and 4-position by straight-chain $C_1$–$C_3$alkylenedioxy (in particular methylenedioxy, ethylenedioxy, 2,2-difluoromethylenedioxy, 2-methoxymethylenedioxy), dihydrobenzofur-5-yl, 2-thienyl, benzofur-2-yl, 2-furyl, 5-chloro- or 5-bromothien-2-yl, 3-methylbenzo[b]thien-2-yl, 1-methylpyrrol-2-yl, 2-thiazolyl, 2-pyridyl which is unsubstituted or substituted by halogen or trifluoromethyl, or 6- or 7-quinolinyl, 6-quinoxalinyl, 2-pyrimidinyl which is mono- to disubstituted by halogen, methyl, trifluoromethyl, cyclopropyl, C₁–C₃alkoxy or methylthio; 4-(2,6-dimethylmorpholinyl);
or R₃ and R₄ together are a 5,6-dihydro-2H-1,4-thiazine ring which is substituted in the 3-position by substituted phenyl, or R₃ and R₄ together are a cyclopentane or tetrahydropyran ring to which an unsubstituted or halogen-substituted benzene ring is fused.

This group will be designated subgroup IDD.

Preferred compounds within the scope of this group IDD are those in which the substituents are defined as follows:

R₁ is C₁–C₂alkyl
R₂ is H, C₁–C₂alkyl, OH, C₁–C₄alkoxy
R₃ is H, C₁–C₂alkyl, cyclopropyl, methoxy, methylthio, methoxymethyl, cyano, trifluoromethyl,
R₄ is monohalophenyl, dihalophenyl, mono-C₁–C₂alkylphenyl, mono-C₁–C₂alkoxyphenyl, 2-naphthyl, 3,4-methylenedioxyphenyl, 3,4-ethylenedioxyphenyl, 2,2-difluoro-5-benzodioxolyl, 2-methoxy-5-benzodioxolyl, 3-(fluoro-C₁–C₂alkoxy)phenyl having 1–3 fluorine atoms, 3-trifluoromethylphenyl, 3,5-bis(trifluoromethyl)phenyl, 4-fluoro-3-trifluoromethylphenyl, 3-fluoro-5-trifluoromethylphenyl, 4-chloro-3-trifluoromethylphenyl, 4-chloro-3-tolyl, monocyanophenyl, 3-cyanomethoxyphenyl, 2-methylthio-5'-trifluoromethylphenyl, 4-methoxy-3-nitrophenyl, 3- or 4-phenoxyphenyl, 3-methylsulfinylmethyl-4-methoxyphenyl, 3-methylsulfonyl-4methoxyphenyl, 3-(prop-1-en-3-yloxy)phenyl, 3-(prop-1-yn-3-yloxy)phenyl, 3-(cyclopropylmethoxy)phenyl, 2,3-dihydrobenzofur-5-yl, 3-trifluoromethyl, 4-chlorobenzyl, 3-trifluoromethylphenoxymethyl, 2-pyridyl, 6-bromo-2-pyridyl, 4-trifluoromethyl-2-pyridyl 6- or 7-quinolinyl, 6-quinoxalinyl, 2-thienyl, 5-chloro- or bromothien-2-yl, 3-methylbenzo[b]thien-2-yl, 2-furyl, benzo[b]fur-2-yl, 1-methylpyrrol-2-yl, 2-thiolyl, 4-(2,6-dimethylmorpholinyl); or R₃ and R₄ together are a 5,6-dihydro-2H-1,4-thiazine ring which is substituted in the 3-position by mono- or dihalophenyl, methoxyphenyl, trifluoromethylphenyl, phenoxy or 3,4-methylenedioxyphenyl, or R₃ and R₄ together are a cyclopentane or tetrahydropyran ring to which an unsubstituted or fluorine-substituted benzene ring is fused.

This group will be designated subgroup IEE. Preferred compounds within this group are those defined as follows:
R₁ is C₁–C₂alkyl,
R₂ is H, methyl,
R₃ is methyl, methoxy, ethyl, methylthio, cyclopropyl,
R₄ is 3-halophenyl, 4-halophenyl, 3-tifluoromethylphenyl, 3-(C₁–C₄haloethoxy)phenyl, 4-fluoro-3-trifluoromethylphenyl, 4-tolyl, 3,4methylenedioxyphenyl, or 3,4-ethylenedioxyphenyl (=subgroup Iee).

Another preferred subgroup within the scope of IDD is that wherein R₁ is C₁–C₂alkyl, R₂ is hydrogen, C₁–C₂alkyl, OH, C₁–C₄alkoxy, R₃ is hydrogen, C₁–C₂alkyl, cyclopropyl, methoxy, methylthio, methoxymethyl, cyano, trifluoromethyl and R₄ is monohalo-monomethoxyphenyl. (=Subgroup Idd).

Among Idd important compounds are those wherein R₄ is 3-halo-4methoxyphenyl. Further preferred compounds within the group Idd are those defined as follows: R₁ is C₁–C₂alkyl, R₂ is hydrogen or methyl, R₃ is methyl, methoxy, ethyl, methylthio, cyclopropyl; and R₄ is 3-halo-4-methoxyphenyl.

A specific group within the scope of the formula I is formed by compounds which are defined as follows:
Z is the group a) where X is oxygen, sulfur, —NH— or —NCH₃,
R₁ is C₁–C₂alkyl,
R₂ is H, methyl,
R₃ is methyl, cyclopropyl and
R₄ is 3-chlorophenyl, 3-trifluoromethylphenyl, 3-trifluoromethoxyphenyl, 4-chlorophenyl.

Another specific group within the scope of the formula I is formed by compounds which are defined as follows:
Z is the group a) where X is oxygen, sulfur, —NH—or —NCH₃,
R₁ is C₁–C₂alkyl,
R₂ is H, methyl,
R₃ is methyl, cyclopropyl and
R₄ is 3-fluor-4-methoxyphenyl.

The invention furthermore relates to a process for the preparation of the compounds according to the invention, to pesticidal, especially microbicidal compositions comprising such compounds as active ingredients, and to the use of such compounds and compositions for preferably controlling phytopathogenic fungi and for preventing attack by fungi.

The iminoethers, iminothioethers and amidines of the general formula

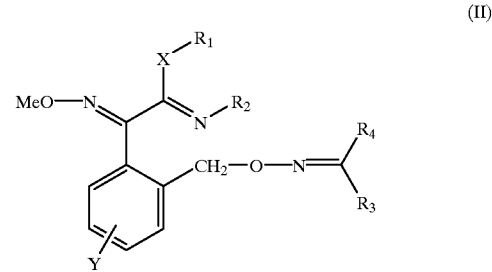

(II)

in which R₁, R₂, R₃, R₄, X and Y are as defined above can be prepared analogously to known methods as they are indicated, for example, in the following references:

"The Chemistry of amidines and imidates" ed. S. Patai, John Wiley & Sons, Vol. 1, 1974 and Vol. 2, 1991, in each case Chapter 7 and 9;

Houben-Weyl "Methoden der organischen Chemie" [Methods in Organic Chemistry], Vol. 8, 1975 and E5, 1985.

For example, imino(thio)ethers of the general formula II in which R₂ is hydrogen and X is oxygen or sulfur and in which R₁, R₃ and R₄ are as defined above can be prepared in accordance with the following equation*

* The following formulae III to XI are to be understood as also comprising the phenylsubstituent Y.

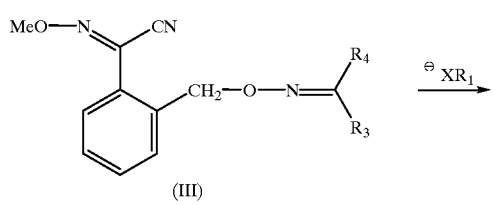

(III)

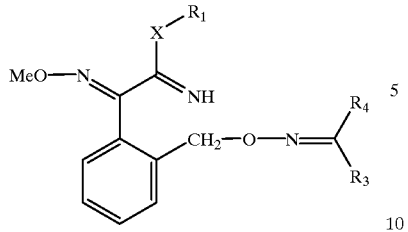
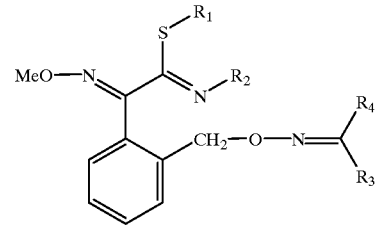

The nitriles of the general formula III in which $R_3$ and $R_4$ are as defined above are reacted with a (thio)alcoholate $R_1X^{\ominus}$ at a temperature between 20° C. and 150° C., if appropriate in an autoclave under pressure. It is expedient to use the corresponding (thio)alcohol or inert organic solvents, for example diethyl ether, dichloromethane, dimethylformamide, tetrahydrofuran or toluene, as diluent.

Furthermore, imino(thio)ethers of the general formula II in which $R_1$ is $C_1$–$C_4$alkyl and X is oxygen or sulfur and in which $R_2$, $R_3$ and $R_4$ are as defined above can be prepared from the (thio)amides of the general formula IV

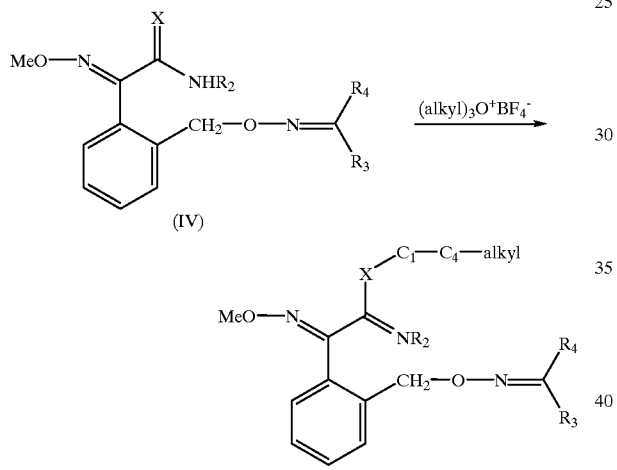

in which X is oxygen or sulfur and in which $R_2$, $R_3$ and $R_4$ are as defined above. To this end, the (thio)amides are reacted with a trialkyloxonium tetrafluoroborate at a temperature from 0° C. to 50° C. in a suitable solvent, for example dichloromethane, chloroform or toluene.

Iminothioethers of the general formula II in which X is sulfur and in which $R_1$, $R_2$, $R_3$ and $R_4$ are as defined above can also be prepared from the thioamides of the general formula V

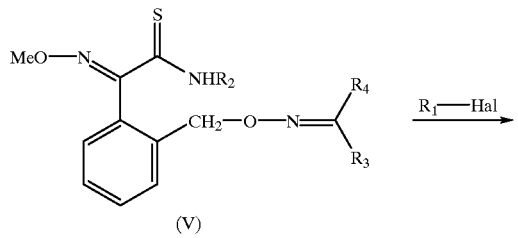

in which $R_2$, $R_3$ and $R_4$ are as defined above. To this end, the thioamides are reacted with halides in the presence of bases, for example potassium carbonate, potassium hydroxide, sodium ethylate and sodium hydride, in a suitable solvent, for example diethyl ether, tetrahydrofuran, dimethylformamide, dimethyl sulfoxide or toluene, at a temperature between 10° C. and 100° C.

Imino(tio)ethers of the general formula II in which $R_2$ is defined as —C(O)$R_5$ and in which $R_3$ and $R_4$ are as defined above can be prepared from the corresponding N-unsubstituted imino(thio)ethers by acylation.

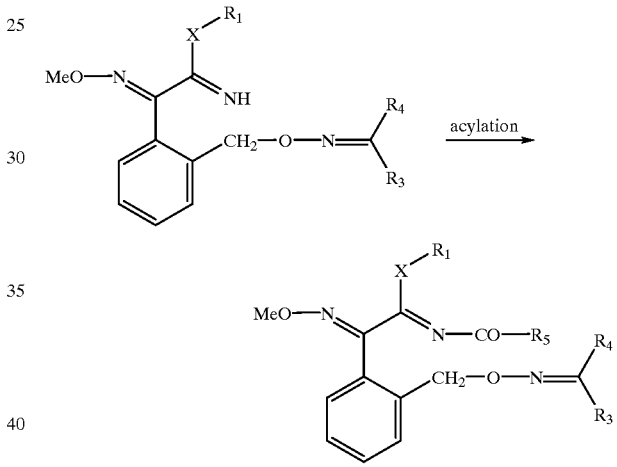

The reaction is carried out in the customary manner using the corresponding acid halides (in particular chlorides and bromides) or chloroformates in the presence of a base or a base mixture composed of triethylamine, pyridine, 4-dimethylaminopyridine and the like in a suitable organic solvent, for example dichloromethane, ethyl acetate, tetrahydrofuran or toluene, in a temperature range between 0° C. and 50° C.

In a further embodiment, imino(thio)ethers and amidines of the general formula II in which X, $R_1$, $R_2$, $R_3$ and $R_4$ are as defined above can be obtained starting from chlorides of the general formula VI in which $R_2$, $R_3$ and $R_4$ are as defined above

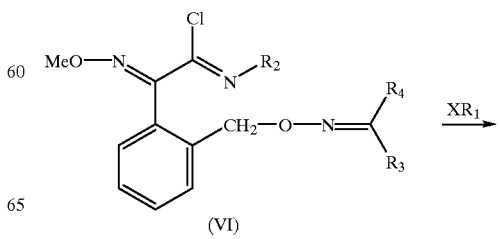

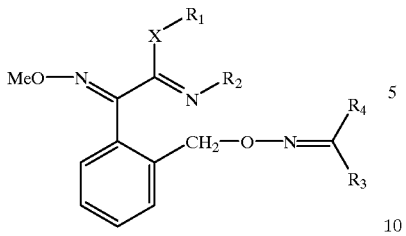

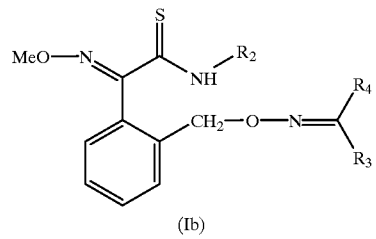

(Ib)

by reaction with (thio)alcoholates or amines in a suitable organic solvent, for example diethyl ether, dichloromethane, dimethylformamide, tetrahydrofuran or toluene, at a temperature between −20° C. and +80° C. The chlorides, in turn, are accessible from the corresponding (thio)amides, for example by reaction with phosphorus oxychloride, thionyl chloride or triphenylphosphine/carbon tetrachloride. See, in this context, C. Ferri, Reaktionen der Organischen Synthese [Reactions in Organic Synthesis]; p. 564, G. Thieme Verlag, Stuttgart 1978.

Amidines of the general formula II in which X is $NR_1$, and $R_1$, $R_2$, $R_3$ and $R_4$ are as defined above can furthermore be prepared from the iminoethers of the general formula VII in which $R_1$, $R_2$, $R_3$ and $R_4$ are as defined above

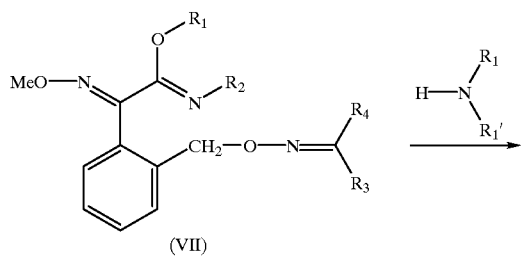

(VII)

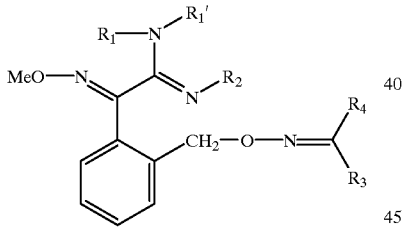

by reaction with a primary or secondary amine in a suitable solvent, for example dichloromethane, dioxane, dimethylformamide or toluene, at a temperature between −20° C. and +60° C.

Thioamides of the general formula Ib can be prepared from the corresponding amides by "sulfur treatment". Substances which can be used for this reaction are, for example, $PS_5$ or Lawesson reagents (see, in this context, Cava & Lawesson, Tetrahedron 41, 5061[1985])

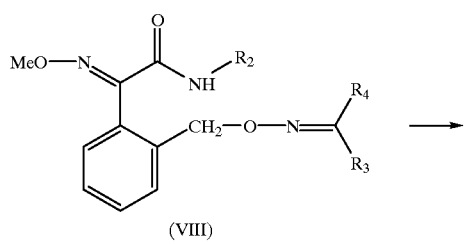

(VIII)

Thioamides of the general formula Ib' can furthermore be obtained from the nitriles of the formula III by an addition reaction with hydrogen sulfide in the presence of a base, for example potassium carbonate, potassium hydroxide or triethylamine, in a suitable solvent, for example dichloromethane, dimethylformamide, chloroform, carbon tetrachloride or tetrahydrofuran. They can, however, also be obtained by the reaction of the nitriles of the formula III with bis(trimethylsilyl)sulfide and sodium methylate (according to P. Y. Lin et al., Synthesis 1992 (12), p. 1219).

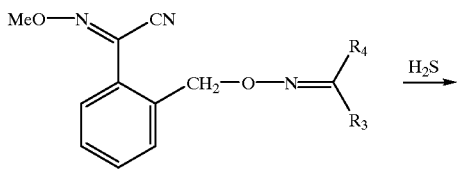

(III)

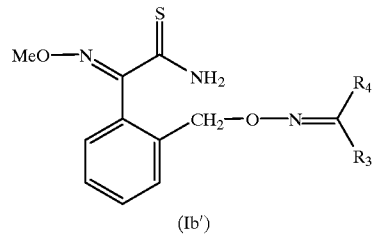

(Ib')

The nitriles of the general formula III can be prepared from compounds of the general formula IX in which U is a leaving group,

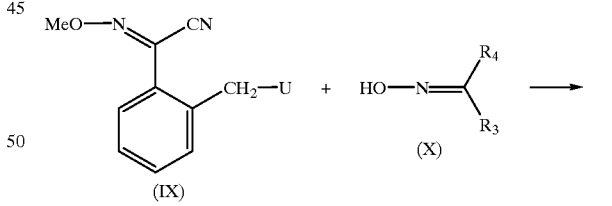

(IX)  (X)

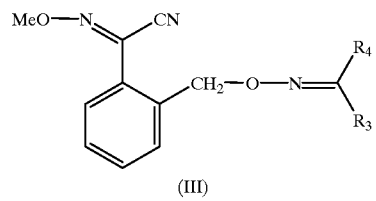

(III)

by reaction with oximes of the general formula X in which $R_3$ and $R_4$ are as defined above. The leaving group U is preferably to be understood as meaning chlorine, bromine, iodine, mesyloxy or tosyloxy. The reaction is carried out, for example, in the presence of a base, such as potassium carbonate, potassium hydroxide, sodium hydride or sodium methylate, in a suitable organic solvent, for example acetone, acetonitrile, dimethylformamide or in tetrahydrofuran, at temperatures between −20° C. and +80° C.

The reaction can also be carried out in a suitable two-phase system (for example water and dichloromethane) in the presence of a phase-transfer catalyst, for example benzyltrimethylammonium chloride.

Important compounds of the formula IX are those in which U is chlorine or bromine. They can be prepared from α-hydroximino-o-tolylacetonitrile, which is known, by O-methylation by means of dimethyl sulfate or methyl iodide in the presence of a base, followed by halogenation, for example by means of N-bromo or N-chlorosuccinimide in boiling carbon tetrachloride.

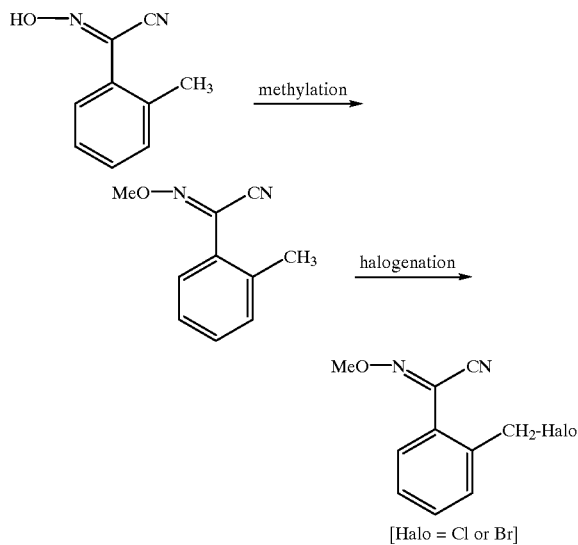

[Halo = Cl or Br]

In a further embodiment, the nitriles of the formula III can be prepared by dehydrating the amides of the general formula XI

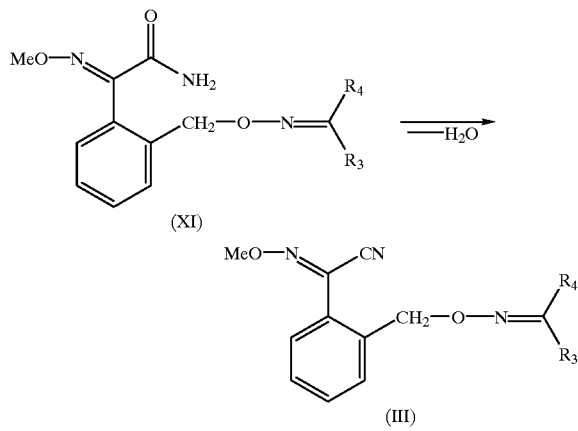

in which $R_3$ and $R_4$ are as defined above. The reaction is carried out for example using trifluoroacetic anhydride in the presence of bases, for example pyridine, triethylamine or potassium carbonate, or by means of the system tertiary phosphane/$CCl_4$ in the presence of tertiary nitrogen bases (see, in this context, R. Appel in Angew. Chem. 87, 869 (1975).

The oximes of the formula X used can be prepared by methods known per se, for example from the corresponding ketones by means of hydroxylamine or a salt thereof, in the presence of a base, for example pyridine. Other methods can be found in Houben-Weyl, Vol. 10/4, p. 3–308 (1968).

Amides of the formula VIII have been disclosed in Patent Publications EP-A-463 488 and WO 92/13830 and can be prepared by the processes described therein.

The invention also relates to the novel imidoyl chlorides of the formula VI in which $R_2$, $R_3$ and $R_4$ are as defined above.

It has now been found that compounds of the formula I, which are distinguished from benzyl oxime ethers from the literature by, inter alia, the novel structural element of the formula $CH_3O-N=C(Z)-$, have a microbicidal spectrum for controlling phytopathogenic microorganisms, in particular fungi, which is particularly useful for practical requirements. They have very advantageous curative, preventive and, in particular, systemic properties and can be used for the protection of a large number of crop plants. Using the active ingredients of the formula I, the pests which occur on plants or parts of plants (fruits, flowers, foliage, stalks, tubers, roots) of various crops of useful plants can be controlled or destroyed, and even parts of plants which are formed at a later stage of growth remain free from phytopathogenic microorganisms.

The compounds of the formula I can furthermore be used as seed-dressing agents for the treatment of seeds (fruits, tubers, grains) and plant cuttings or other propagation material for the protection against fungal infections and against soil-borne phytopathogenic fungi.

Compounds of the formula I are active for example against phytopathogenic fungi which belong to the following classes: *Fungi imperfecti* (in particular Botrytis, Pyricularia, Helminthosporium, Fusarium, Septoria, Cercospora, Cercosporella and Alternaria); Basidiomycetes (for example Rhizoctonia, Hemileia, Puccinia). Moreover, they are active against the class of the Ascomycetes (for example Venturia and Erysiphe, Podosphaera, Monilinia, Uncinula), but mainly also against the class of the Oomycetes (for example Phytophthora, Peronospora, Bremia, Pythium, Plasmopara).

Target crops for the crop-protecting use disclosed herein are, within the scope of this invention, for example the following types of plants: cereals (wheat, barley, rye, oats, triticale, rice, maize, sorghum and related species); beet (sugar and fodder beet); pome fruit, stone fruit and soft fruit (apples, pears, plums, peaches, almonds, cherries, strawberries, gooseberries, raspberries and blackberries); pulses (beans, lentils, peas, soya beans); oil crops (rape, mustard, poppy, olives, sunflowers, coconut, castor, cocoa, groundnuts); cucurbits (pumpkin, cucumbers, melons); fibre plants (cotton, flax, hemp, jute); citrus fruit (oranges, lemons, grapefruit, tangerines); vegetables (spinach, lettuce, asparagus, cabbages, carrots, onions, tomatoes, potatoes, bell pepper); the laurel family (avocado, cinnamon, camphor), or plants such as tobacco, nuts, coffee, sugarcane, tea, pepper and other spice plants, grapevine, hops, eggplants, the banana family, latex plants and ornamentals.

Active ingredients of the formula I are customarily used in the form of combinations and can be applied to the plant or the area to be treated simultaneously or in succession with other active ingredients. These other active ingredients can be fertilizers, trace element mediators or other preparations which have an effect on plant growth. Selective herbicides and insecticides, fungicides, bactericides, nematicides, molluscicides or mixtures of a plurality of these preparations, with or without other carriers conventionally used in the art of formulation, surfactants or other application-enhancing additives, can also be used.

Suitable carriers and additives can be solid or liquid and are those substances which are expedient in the art of formulation, for example natural or regenerated mineral substances, solvents, dispersants, wetting agents, tackifiers, thickeners, binders or fertilizers.

The following are possible as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethyl ether, ketones, such as cyclohexanone, strongly polar solvents, such as N-methyl-2-pyrrolidone, dimethyl sulfoxide or dimethylformamide, and also epoxidized or unepoxidized vegetable oils, such as epoxidized coconut oil or soya oil; or water.

Solid carriers which are generally used, for example for dusts and dispersible powders, are ground natural rocks, such as calcite, talc, kaolin, montmorillonite or attapulgite. Particularly expedient application-enhancing additives which may result in a greatly reduced rate of application, are, moreover, natural (animal or vegetable) or synthetic phospholipids from the series of the cephalins and lecithins, which can be obtained from, for example, soya beans.

Suitable surface-active compounds are non-ionic, cationic and/or anionic surfactants which have good emulsifying, dispersing and wetting properties, depending on the nature of the active ingredient of the formula I to be formulated. Surfactants are also to be understood as meaning mixtures of surfactants.

Suitable anionic surfactants can be either so-called water-soluble soaps or water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the sodium or potassium salts of oleic or stearic acid, or of natural mixtures of fatty acids which can be obtained from, for example, coconut oil or tallow oil. Mention must also be made of the fatty acid methyl taurinates.

Possible non-ionic surfactants are polyglycol ether derivatives of aliphatic or cycloaliphatic alcohols, saturated or unsaturated fatty acids and alkylphenols, which can have 3 to 30 glycol ether groups and 8 to 20 carbon atoms in the (aliphatic) hydrocarbon radical and 6 to 18 carbon atoms in the alkyl radical of the alkylphenols.

Examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Moreover, fatty acid esters of polyoxyethylene sorbitan, such as polyoxyethylene sorbitan trioleate, are also suitable.

The cationic surfactants are mainly quaternary ammonium salts which have, as N-substituent, at least one alkyl radical having 8 to 22 C atoms and, as further substituents, lower, halogenated or free alkyl, benzyl or lower hydroxyalkyl radicals.

The anionic, non-ionic or cationic surfactants conventionally used in the art of formulation are known to the expert or can be found in the relevant specialist literature:

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" [Surfactants Guide], Carl Hanser Verlag, Munich/Vienna 1981.

As a rule, the agrochemical preparations comprise 0.1 to 99%, in particular 0.1 to 95%, of active ingredient of the formula I, 99.9 to 1%, in particular 99.9 to 5%, of a solid or liquid additive, and 0 to 25%, in particular 0.1 to 25%, of a surfactant.

While concentrated compositions are more preferred as commercial products, the end user will, as a rule, use dilute compositions.

The compositions can also comprise other additives, such as stabilizers, antifoams, viscosity regulators, binders, tackifiers and fertilizers or other active ingredients for achieving specific effects.

The formulations, i.e. the compositions, preparations or combinations comprising the active ingredient of the formula I and, if appropriate a solid or liquid additive, are produced in a known manner, for example by intimately mixing and/or grinding the active ingredient with an extender, for example a solvent (mixture), a solid carrier material and, if appropriate, surface-active compounds (surfactants).

A preferred process for applying an active ingredient of the formula I, or an agrochemical composition comprising at least one of these active ingredients, is applying to the foliage (foliar application). Frequency of application and rate of application both depend on the danger of attack by the pathogen in question. However, the active ingredients of the formula I can also reach the plant via the soil through the root system (systemic action) by drenching the locus of the plant with a liquid composition or by incorporating the substances into the soil in solid form, for example in the form of granules (soil application). In the case of paddy rice, such granules can be metered out into the flooded rice field. Alternatively, the compounds of the formula I can be applied to seed kernels (coating), either by soaking the kernels in a liquid preparation of the active ingredient or by coating them with a solid preparation. In principle, any type of plant propagation material can be protected using compounds of the formula I, for example seeds, roots or stalks.

The compounds of the formula I are used as pure compounds or, preferably, together with the auxiliaries conventionally used in the art of formulation. To this end, they are advantageously processed in the known manner, for example to give emulsifiable concentrates, spreadable pastes, directly sprayable or dilutable solutions, dilute emulsions, wettable powders, soluble powders, dusts, granules, and encapsulations, for example in polymeric substances. The methods of application, such as spraying, atomizing, dusting, scattering, brushing on or pouring, as well as the nature of the compositions are selected to suit the intended aims and the prevailing circumstances. Favourable rates of application are, generally, 5 g to 2 kg of active ingredient (AI) per ha, preferably 25 g to 800 g of AI/ha and, particularly preferably, 50 g to 400 g of AI/ha. When used as seed-dressing products, dosage rates of 0.001 g to 1.0 g of active ingredient are advantageously used per kg of seeds.

The examples which follow are intended to illustrate the invention in greater detail without imposing any restriction thereto.

Preferred fungicides are Nos. 1.13; 1.331; 1.332; 2.10; 2.57; 2.101; 2.115; 2.119–2.122; 3.11; 3.101; 3.102; 3.104–3.105; 3.107–3.109; 4.10; 4.11; 4.12; 4.51; 4.93 as well as the compounds in Examples H-1, H-2 and H-4.

Preparation Examples

EXAMPLE H-1

Preparation of

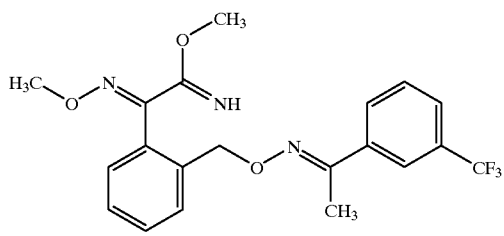

A solution of 1.42 g of 2-[2-(methyl(3-trifluoromethylphenyl)oximinomethyl)phenyl]-2-methoximinoacetamide in 5 ml of dichloromethane is added in the course of 10 minutes at room temperature to 670 mg of trimethyloxonium tetrafluoroborate in 5 ml of dichloromethane with stirring. The reaction mixture is stirred for 18 hours, then diluted with 150 ml of dichloromethane and washed in succession with in each case 100 ml of 10-per cent sodium carbonate solution and half-saturated sodium chloride solution. The aqueous phases are re-extracted using 150 ml of dichloromethane and the combined organic phases are dried over anhydrous sodium sulfate and concentrated. The yellow oily residue is purified by chromatography on silica gel using hexane/ethyl acetate (6:4) as the eluent. This gives O-methyl-2-[2-(methyl(3-trifluoromethylphenyl)-oximinomethyl)phenyl] 2-methoximinoacetimidate as an oil; MS: $M^+$ 407(11), 116(100).

EXAMPLE H-2

Preparation of

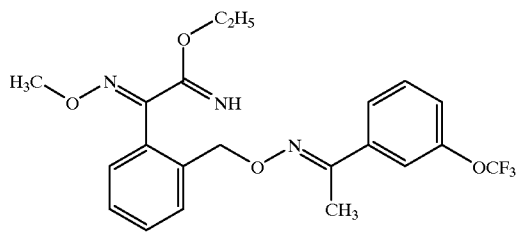

A solution of 1.64 g of 2-[2-(methyl(3-trifluoromethoxyphenyl)oximinomethyl)phenyl]-2-methoximinoacetamide in 5 ml of dichloromethane is added in the course of 5 minutes at room temperature to a solution of 912 mg of triethyloxonium tetrafluoroborate in 5 ml of dichloromethane with stirring. After 7 hours, a further 190 mg of triethyloxonium tetrafluoroborate are added. After 16 hours, the reaction mixture is poured into 100 ml of 10per cent sodium carbonate solution and extracted using 2×200 ml of dichloromethane. The organic phases are dried over anhydrous sodium sulfate and concentrated. The orange oily residue is purified by chromatography on silica gel using hexane/ethyl acetate (7:3) as the eluent. This gives O-ethyl-2-[2-methyl(3-trifluoromethoxyphenyl)-oximinomethyl)phenyl] 2-methoximinoacetimidate as an oil; MS: $M^+$ 437 (11), 116(100).

EXAMPLE H-3

Preparation of

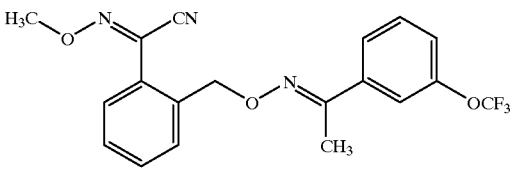

0.66 g of m-trifluoromethoxyacetophenone oxime are introduced into 5 ml of acetonitrile, and 0.62 g of anhydrous potassium carbonate are added. A solution of 0.76 g of α-methoximino-2-bromomethylphenylacetonitrile in 5 ml of acetonitrile is then added in one portion at room temperature. After the mixture has been stirred for 5 hours, it is diluted using 50 ml of ethyl acetate, and the reaction mixture is washed twice using 30 ml of saturated sodium chloride solution. Each of the aqueous phases is re-extracted using 50 ml of ethyl acetate in each case. The combined organic phases are dried over anhydrous magnesium sulfate and concentrated. The reddish brown oily residue is purified by chromatography on silica gel using hexane/ethyl acetate (9:1) as the eluent. This gives 2-[2(methyl(3-trifluoromethoxyphenyl)oximinomethyl)phenyl]-2-methoximinoacetonitrile as an oil; MS: $M^+$391(1), 360(10), 202(25), 189(37), 173(100), 142(54). The starting material can be prepared as follows:

58 g of potassium carbonate and 42.38 g of dimethyl sulfate are added in succession to a solution of 44.85 g of α-hydroximino-o-tolylacetonitrile in 500 ml of acetone. In the course of this process, the reaction temperature rises to approximately 50°. After the mixture has been stirred for 30 minutes, it is filtered, and the filtrate is concentrated. The residue is diluted with 500 ml of ethyl acetate and washed twice using 300 ml of saturated sodium chloride solution. Each of the aqueous phases is re-extracted using 400 ml of ethyl acetate. The combined organic phases are dried over magnesium sulfate and concentrated.

The brown oily residue is purified by chromatography on silica gel using hexane/ethyl acetate (9:1) as the eluent. This gives [E]-α-methoximino-o-tolylacetonitrile as an oil; MS: $M^+$ 174(16), 143(43), 116(100); $^1$H NMR δ(CDCl$_3$): 2.51 (s, 3H), 4.20 (s, 3H), 7.22–5.51 (m, 3H), 7.52–7.58 (m, 1H).

1 spatula tipful of dibenzoyl peroxide is added to a boiling solution of 7.84 g of [E]-α-methoximino-o-tolylacetonitrile in 100 ml of carbon tetrachloride, followed by an addition of 8.01 g of N-bromosuccinimide, in portions, in the course of 10 minutes. After a reaction time of 6 hours, the mixture is filtered, and the filtrate is evaporated on a rotary evaporated. The orange oily residue is purified by chromatography on silica gel using hexane/ethyl acetate (9:1) as the eluent. This gives [E]-α-methoximino-2-bromomethyl-phenylacetonitrile as an oil; MS: $M^+$ 252/254(4), 221/223 (10), 173(56), 142(100); $^1$H NMR δ(CDCl$_3$): 4,27 (s, 3H), 4.79 (s, 2H), 7.39–7.52 (m, 3H), 7.64–7.72 (m, 1H).

EXAMPLE H-4

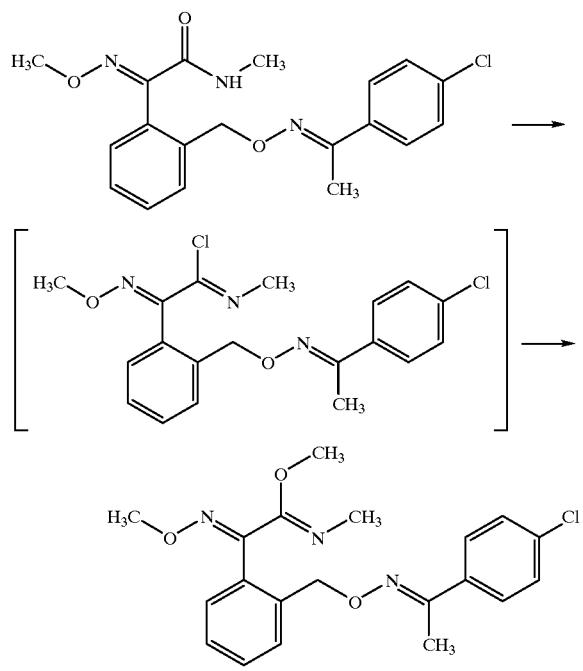

3.74 g of N-methyl-2-[2-(methyl(4-chlorophenyl) oximinomethyl)phenyl]-2-methoximinoacetamide and 3.4 g of triphenylphosphine are dissolved in 15 ml of acetonitrile at approximately 40°. The mixture is then cooled to 10°, and 1.1 ml of carbon tetrachloride are added to the white suspension. After 45 minutes, a yellow solution is formed, and stirring is continued for 3 hours at room temperature. The resulting solution of the unstable imidoyl chloride (16 g) is reacted further directly without further purification.

8 g of the solution of the imidoyl chloride which has been prepared above are added to a solution of 8.1 mmol of sodium methylate in 8 ml of methanol in the course of 2 minutes at 5°. The yellow emulsion is stirred for 30 minutes at room temperature and then stirred into 80 ml of water. The mixture is extracted using 2×60 ml of ethyl acetate, and the extracts are dried and concentrated on a rotary evaporater. The yellowish oily-crystalline residue is purified by chromatography on silica gel using hexane/ethyl acetate (8:2) as the eluent. This gives N,O-dimethyl-2-[2-(methyl(4-chlorophenyl)oximinomethyl)phenyl] 2-methoximinoacetimidate of melting point 79–80° C.

EXAMPLE H-5

(Compound No. 4.51)

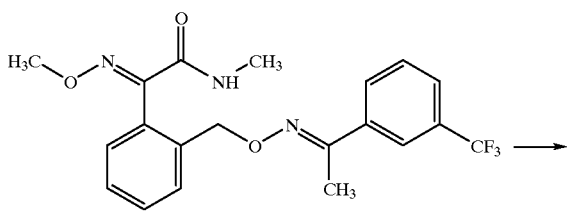

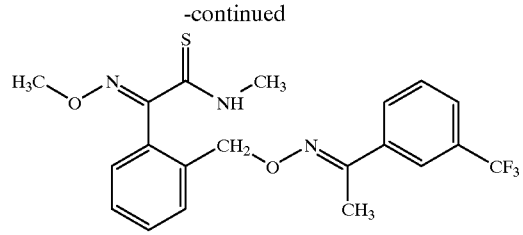

4.45 g of Lawesson reagent are added to a solution of 4.07 g of N-methyl-2-[2-(methyl(3-trifluoromethylphenyl) oximinomethyl)phenyl] 2-methoximinoacetamide in 50 ml of toluene, with stirring, and the suspension which forms is subsequently heated for 2 hours at 80° C. After the solvent has been distilled off, the dark yellow oil obtained is separated by chromatography on silica gel using hexane/ethyl acetate. This gives N-methyl-2-[2-(methyl(3-trifluoromethylphenyl)oximinomethyl)phenyl]-2-methoximinothioacetamide as yellow oil which crystallizes; melting point 100–106° C.

EXAMPLE H-6

(Compound No. 2.57)

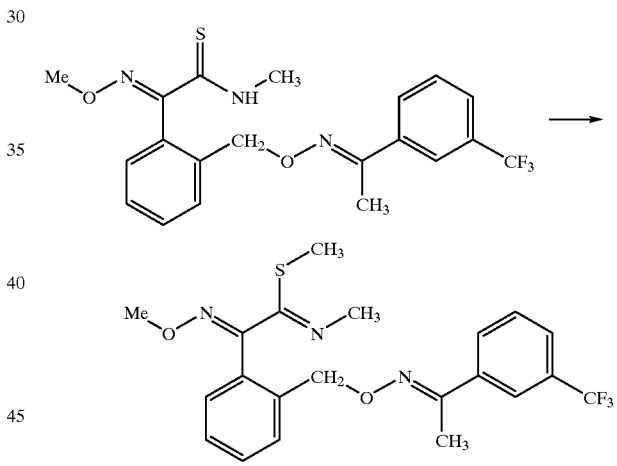

A solution of 0.172 ml of methyl iodide in 2 ml of dimethylformamide is added at room temperature to a yellow suspension of 1.06 g of N-methyl-2-[2-(methyl(3-trifluoromethylphenyl)oximinomethyl)phenyl] 2-methoximinothioacetamide and 346 mg of potassium carbonate in 8 ml of dimethylformamide, with stirring. After the reaction mixture has been heated for 1.5 hours at 80° C., it is poured into 100 ml of ice-water and extracted using 2×150 ml of ethyl acetate. The organic phases are washed using 100 ml of water, combined, dried and concentrated on a rotary evaporater. The pale brown oil obtained is purified by chromatography on silica gel using hexane/ethyl acetate (85:15) as the eluent. N,S-Dimethyl-2-[2-(methyl(3-trifluoromethylphenyl)oximinomethyl)phenyl] 2-methoximinothioacetimidate is obtained as an oil. MS: M$^+$ 437(1), 406(8), 390(15), 251(20), 221(52), 205(54), 186 (100), 145(36), 116(87), 88(45).

EXAMPLE H-7
(Compound No. 3.101)

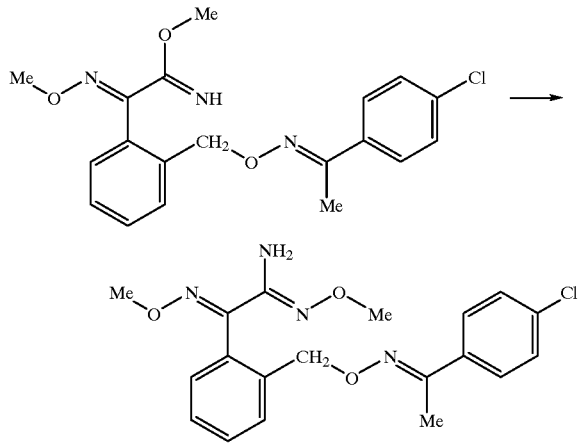

3.36 g of O-methylhydroxylamine hydrochloride are added to a solution of 3.74 g of O-methyl-2-[2-(methyl{4-chlorophenyl}oximinomethyl)phenyl]-2-methoximino-acetimidate date in 30 ml of dimethylformamide (DMF). Thereafter 8.28 g of finely ground potassium carbonate are added in one portion, the temperature in the mixture thereby rising to 32° C.

After stirring at room temperature for 2 hours the reaction mixture is poured into water and twice extracted with 50 ml each of ethylacetate. The combined extracts are dried with magnesium sulfate and evaporated. Crude O-methylamideoximether is obtained in form of a colourless oil. MS: $M^+$ 388 (0.4), 236 (100). The oil solidifies, m.p. 76–78° C.

EXAMPLE H-8
(Compound No. 3.102)

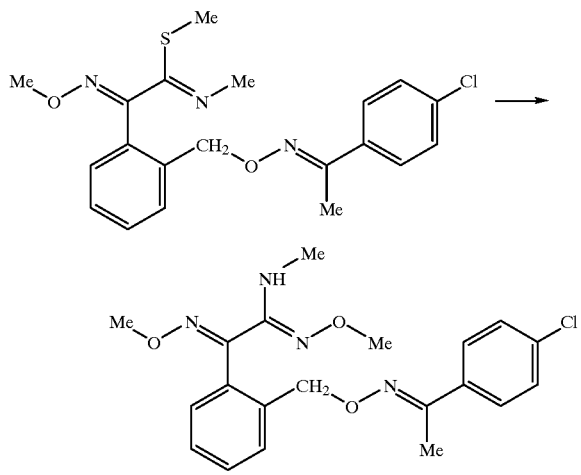

0.84 g of O-methylhydroxylamine hydrochloride are added to a solution of 1.0 g of N,S-dimethyl-2-[2-(methyl-{4-chlorophenyl}oximinomethyl)phenyl]-2-methoximino-thio-acetimidate in 8 ml DMF and thereafter 2.07 g of finely ground potassium carbonate are added thereto, the temperature in the mixture thereby rising to 32° C. After stirring of the mixture at room temperature for 1.5 hours the reaction mixture is poured into 80 ml of ice water and is extracted three times with 25 ml each of ethyl acetate. The combined extracts are washed with water, dried with sodium sulfate and evaporated. The thus obtained yellowish oil is purified by flash chromatography on silica gel using hexane/ethyl acetate (80:20) as the eluent. The desired N,O-dimethylamidoxime ether is obtained in form of a clear highly viscous oil. MS: $M^+$ 402 (2), 250 (100).

EXAMPLE H-9
(Compound No. 3.11)

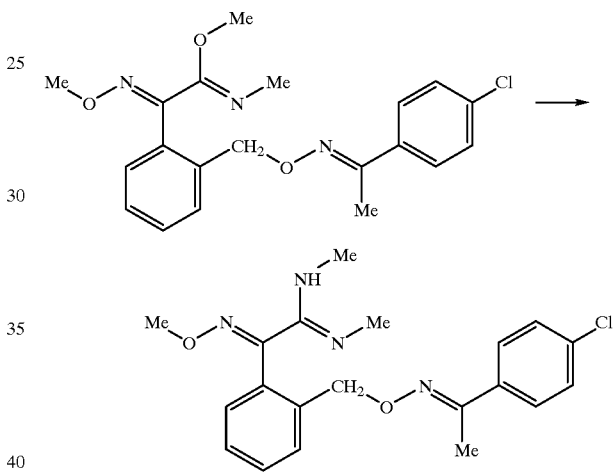

1,0 g of N,O-dimethyl-2-[2-(methyl{4-chlorophenyl}oximinomethyl)phenyl]-2-methoximino-acetimidate are added to a solution consisting of 3 ml of methanol and 2.0 g methylamine in methanol (37%). The resulting suspension is stirred at room temperature for 24 hours. The oil obtained is mixed with 30 ml of acetone and filtered on 20 g silica gel. The silica gel with adsorbed endproduct on it is eluated with a mixture of 100 ml acetone and 5 ml triethylamine. The eluate is evaporated and dried by high vacuum. The desired N,N'-dimethylamidine is obtained as colourless highly viscous oil. MS: $M^+$ 386 (3.2), 71 (100), 204 (91).

The following compounds can be prepared in this manner or by one of the methods indicated above:

TABLE 1

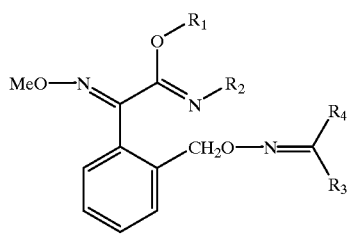

[Rhodano = thiocyano]

| Ex. No. | $R_1$ | $R_2$ | $R_3$ | $R_4$ | Physical data MS: molecular peak (%), base peak |
|---|---|---|---|---|---|
| 1.1 | Me | H | Me | Phenyl | |
| 1.2 | Me | Me | Me | Phenyl | |
| 1.3 | Me | H | H | 2-Fluorophenyl | |
| 1.4 | Me | Me | Me | 2-Fluorophenyl | |
| 1.5 | Me | H | Me | 3-Fluorophenyl | |
| 1.6 | Me | Me | Me | 3-Fluorophenyl | |
| 1.7 | Me | H | Me | 4-Fluorophenyl | |
| 1.8 | Me | H | cyclopropyl | 4-Fluorophenyl | |
| 1.9 | Me | H | H | 2-Chlorophenyl | |
| 1.10 | Me | H | Me | 3-Chlorophenyl | |
| 1.11 | Me | H | cyclopropyl | 3-Chlorophenyl | |
| 1.12 | Et | H | Me | 3-Chlorophenyl | |
| 1.13 | Me | H | Me | 4-Chlorophenyl | m.p. 73–75° C. |
| 1.14 | Et | Me | Me | 4-Chlorophenyl | oil; 401(1), 58 |
| 1.15 | Allyl | Me | Me | 4-Chlorophenyl | |
| 1.16 | —CH₂—C≡CH | Me | Me | 4-Chlorophenyl | |
| 1.17 | Phenyl | Me | Me | 4-Chlorophenyl | |
| 1.18 | Benzyl | Me | Me | 4-Chlorophenyl | |
| 1.19 | Me | H | Me | 2-Bromophenyl | |
| 1.20 | Me | H | Me | 3-Bromophenyl | |
| 1.21 | Me | Me | Me | 3-Bromophenyl | |
| 1.22 | Me | H | Me | 4-Bromophenyl | |
| 1.23 | Me | H | cyclopropyl | 4-Bromophenyl | |
| 1.24 | Me | H | cyclopropyl | 4-Chlorophenyl | oil; 399(1), 58 |
| 1.25 | Me | Me | cyclopropyl | 4-Chlorophenyl | |
| 1.26 | Me | H | CH₃S | 4-Chlorophenyl | |
| 1.27 | Me | H | CH₃O | 4-Chlorophenyl | |
| 1.28 | Me | H | CH₃OCH₂ | 4-Chlorophenyl | |
| 1.29 | Me | H | CH₃SCH₂ | 4-Chlorophenyl | |
| 1.30 | Me | H | CF₃ | 4-Chlorophenyl | |
| 1.31 | Me | H | CN | 4-Chlorophenyl | |
| 1.32 | Me | H | Et | 4-Chlorophenyl | |
| 1.33 | Me | H | Propyl | 4-Chlorophenyl | |
| 1.34 | Me | H | i-Propyl | 4-Chlorophenyl | |
| 1.35 | Me | H | Me | 2,4-Difluorophenyl | |
| 1.36 | Me | Me | Me | 3,4-Difluorophenyl | |

TABLE 1-continued

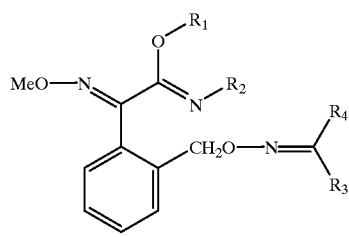

[Rhodano = thiocyano]

| | | | | |
|---|---|---|---|---|
| 1.37 | Me | H | Me | 2,3-Difluorophenyl |
| 1.38 | Me | Me | Me | 3,4-Difluorophenyl |
| 1.39 | Me | H | Me | 2,5-Difluorophenyl |
| 1.40 | Me | Me | Me | 3,5-Difluorophenyl |
| 1.41 | Me | H | Me | 2,4-Dichlorophenyl |
| 1.42 | Me | Me | Me | 3,4-Dichlorophenyl |
| 1.43 | Me | H | Me | 2,5-Dichlorophenyl |
| 1.44 | Me | Me | Me | 3,5-Dichlorophenyl |
| 1.45 | Me | H | Me | 3-Cl,4-F-Phenyl |
| 1.46 | Me | Me | Me | 3-Cl,4-F-Phenyl |
| 1.47 | Me | H | Me | 4-Cl,2-F-Phenyl |
| 1.48 | Me | H | Me | 2,3,4-Trifluorophenyl |
| 1.49 | Me | Me | Me | 2,3,6-Trifluorophenyl |
| 1.50 | Me | H | Me | 2,4,6-Trifluorophenyl |
| 1.51 | Me | Me | Me | 2,4,5-Trifluorophenyl |
| 1.52 | Me | OH | Me | 4-Chlorophenyl |
| 1.53 | Me | OMe | Me | 4-Chlorophenyl |
| 1.54 | Me | H | Me | 2,3,4-Trichlorophenyl |
| 1.55 | Me | Me | Me | 3,4,5-Trichlorophenyl |
| 1.56 | Me | H | Me | 2,4,5-Trichlorophenyl |
| 1.57 | Me | Me | Me | 1-Naphthyl |
| 1.58 | Me | H | Me | 2-Naphthyl |
| 1.59 | Me | H | cyclopropyl | 2-Naphthyl |
| 1.60 | Me | Me | Me | 2-Naphthyl |
| 1.61 | Me | Me | cyclopropyl | 2-Naphthyl |
| 1.62 | Me | H | Me | 2-Methylphenyl |
| 1.63 | Me | Me | Me | 3-Methylphenyl |
| 1.64 | Me | H | Me | 4-Methylphenyl |
| 1.65 | Me | Me | Me | 4-Methylphenyl |
| 1.66 | Me | H | cyclopropyl | 4-Methylphenyl |
| 1.67 | Me | H | Me | 2,3-Dimethylphenyl |
| 1.68 | Me | Me | Me | 2,4-Dimethylphenyl |
| 1.69 | Me | H | Me | 2,5-Dimethylphenyl |
| 1.70 | Me | Me | Me | 3,4-Dimethylphenyl |
| 1.71 | Me | H | Me | 3,5-Dimethylphenyl |
| 1.72 | Me | Me | Me | 2-Methoxyphenyl |
| 1.73 | Me | H | Me | 3-Methoxyphenyl |
| 1.74 | Me | Me | Me | 3-Methoxyphenyl |
| 1.75 | Me | Et | Me | 3-Methoxyphenyl |
| 1.76 | Et | Me | Me | 3-Methoxyphenyl |
| 1.77 | Et | Et | Me | 3-Methoxyphenyl |
| 1.78 | Me | H | Me | 4-Methoxyphenyl |
| 1.79 | Me | H | Me | 3,4-Dimethoxyphenyl |
| 1.80 | Me | Me | Me | 3,5-Dimethoxyphenyl |
| 1.81 | Me | H | Me | 3,4-Methylenedioxyphenyl |
| 1.82 | Me | Me | Me | 3,4-Methylenedioxyphenyl |
| 1.83 | Me | H | cyclopropyl | 3,4-Methylenedioxyphenyl |

TABLE 1-continued

[Rhodano = thiocyano]

| # | R1 | R2 | R3 | R4 | |
|---|---|---|---|---|---|
| 1.84 | Me | Me | cyclopropyl | 3,4-Methylenedioxyphenyl | |
| 1.85 | Me | H | SMe | 3,4-Methylenedioxyphenyl | |
| 1.86 | Me | Me | SMe | 3,4-Methylenedioxy-phenyl | oil; 429(11), 72 |
| 1.87 | Me | H | OMe | 3,4-Methylenedioxyphenyl | |
| 1.88 | Me | H | Me | 3,4-Ethylenedioxyphenyl | |
| 1.89 | Me | Me | Me | 3,4-Ethylenedioxyphenyl | |
| 1.90 | Me | H | cyclopropyl | 3,4-Ethylenedioxyphenyl | |
| 1.91 | Me | Me | cyclopropyl | 3,4-Ethylenedioxyphenyl | |
| 1.92 | Me | H | Me | 2,2-Difluoro-5-benzodioxolyl | |
| 1.93 | Me | Me | Me | 2,2-Difluoro-5-benzodioxolyl | |
| 1.94 | Me | H | Et | 2,2-Difluoro-5-benzodioxolyl | |
| 1.95 | Me | H | Me | 3-Difluoromethoxyphenyl | |
| 1.96 | Me | H | Me | 4-Difluoromethoxyphenyl | |
| 1.97 | Me | Me | Me | 3-Difluoromethoxyphenyl | |
| 1.98 | Me | H | Me | 3-(2,2,2-Trifluoroethoxy)phenyl | |
| 1.99 | Me | Me | Me | 3-(1,1,2,2-Tetrafluoroethoxy)-phenyl | |
| 1.100 | Me | H | Me | 3-(1,1,2,3,3,3-Hexafluoro-propoxy)phenyl | |
| 1.101 | Me | H | Me | 4-(2,2,2-Trifluoroethoxy)phenyl | |
| 1.102 | Me | H | Me | 4-(1,1,2,2-Tetrafluoroethoxy)-phenyl | |
| 1.103 | Me | OH | Me | 3-Trifluoromethoxyphenyl | |
| 1.104 | Me | Me | Me | 3-Trifluoromethoxyphenyl | |
| 1.105 | Me | OMe | Me | 3-Trifluoromethoxyphenyl | |
| 1.106 | Me | COCH$_3$ | Me | 3-Trifluoromethoxyphenyl | |
| 1.107 | Me | COOCH$_3$ | Me | 3-Trifluoromethoxyphenyl | |
| 1.108 | Me | H | Me | 4-Trifluoromethoxyphenyl | |
| 1.109 | Me | Me | Me | 2-Trifluoromethylphenyl | |
| 1.110 | Me | H | Me | 4-Trifluoromethylphenyl | |
| 1.111 | Me | Et | Me | 3-Trifluoromethylphenyl | |
| 1.112 | Me | Me | Me | 3-Trifluoromethylphenyl | oil; 421(2), 72 |
| 1.113 | Me | H | cyclopropyl | 3-Trifluoromethylphenyl | |
| 1.114 | Me | H | Et | 3-Trifluoromethylphenyl | |
| 1.115 | Me | H | CN | 3-Trifluoromethylphenyl | |
| 1.116 | Me | H | OMe | 3-Trifluoromethylphenyl | oil; 423(1), 58 |
| 1.117 | Me | Me | OMe | 3-Trifluoromethylphenyl | oil; 473(1), 72 |
| 1.118 | Me | Me | SMe | 3-Trifluoromethylphenyl | |
| 1.119 | Me | H | CH$_2$OCH$_3$ | 3-Trifluoromethylphenyl | |
| 1.120 | Me | OH | Me | 3-Trifluoromethylphenyl | |
| 1.121 | Me | OMe | Me | 3-Trifluoromethylphenyl | |
| 1.122 | Me | COCH$_3$ | Me | 3-Trifluoromethylphenyl | |
| 1.123 | Me | COOCH$_3$ | Me | 3-Trifluoromethylphenyl | |
| 1.124 | Me | H | Me | 3,5-Bis(trifluoromethyl)phenyl | |
| 1.125 | Me | H | Me | 4-F,3-CF$_3$-phenyl | |
| 1.126 | Me | Me | Me | 4-F,3-CF$_3$-phenyl | |

TABLE 1-continued

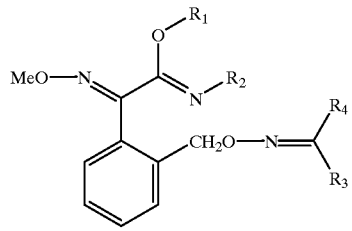

[Rhodano = thiocyano]

| # | R1 | R2 | R3 | R4 | |
|---|----|----|----|----|---|
| 1.127 | Me | Me | cyclopropyl | 4-F,3-CF$_3$-phenyl | |
| 1.128 | Me | H | Me | 2-Cl,5-CF$_3$-phenyl | |
| 1.129 | Me | H | Me | 3-Acetylphenyl | |
| 1.130 | Me | Me | Me | 4-Acetylphenyl | |
| 1.131 | Et | H | Me | 3-Carboxyphenyl | |
| 1.132 | Me | H | Me | 4-Carboxyphenyl | |
| 1.133 | Me | Me | Me | 3-Carbethoxyphenyl | |
| 1.134 | Me | H | Me | 4-Carbethoxyphenyl | |
| 1.135 | Et | H | Me | 2-Cyanophenyl | |
| 1.136 | Me | H | Me | 3-Cyanophenyl | |
| 1.137 | Me | Me | Me | 4-Cyanophenyl | |
| 1.138 | Me | H | Me | 3-Cyanomethylphenyl | |
| 1.139 | Me | Me | Me | 3-Cyanomethoxyphenyl | |
| 1.140 | Me | H | Me | 4-Cyanomethylphenyl | |
| 1.141 | Me | H | Me | 4-Cyclohexylphenyl | |
| 1.142 | Me | H | Me | 4-Biphenylyl | |
| 1.143 | Me | Me | Me | 2-Fluorenyl | |
| 1.144 | Me | H | Me | 3-Benzyloxyphenyl | |
| 1.145 | Me | Me | Me | 4-Benzyloxyphenyl | |
| 1.146 | Me | H | Me | 3,5-Dibenzyloxyphenyl | |
| 1.147 | Me | H | Me | 4-Bromo-2-fluorophenyl | |
| 1.148 | Me | Me | Me | 4-Bromo-3-methylphenyl | |
| 1.149 | Me | H | Me | 6-(2,2-Difluoro-1,4-benzo-dioxanyl) | |
| 1.150 | Me | Me | Me | 6-(2,2,3-Trifluoro-1,4-benzodioxanyl) | |
| 1.151 | Me | H | Me | Pentafluorophenyl | |
| 1.152 | Me | Me | Me | 3-F,5-CF$_3$-phenyl | |
| 1.153 | Me | Me | Me | 3-OMe,5-CF$_3$-phenyl | |
| 1.154 | Me | H | Me | 3-NO$_2$,5-CF$_3$-phenyl | |
| 1.155 | Me | Me | Me | 4-Br,3-CF$_3$-phenyl | |
| 1.156 | Me | H | Me | 4-tert-Butylphenyl | |
| 1.157 | Me | Me | Me | 4-sec-Butylphenyl | |
| 1.158 | Me | Me | Me | 4-Butylphenyl | |
| 1.159 | Me | Me | Me | 4-Butoxyphenyl | |
| 1.160 | Me | H | Me | 3-F,4-MeO-phenyl | oil; 387(19), 58 |
| 1.161 | Me | H | Me | 3-Cl,4-MeO-phenyl | |
| 1.162 | Me | Me | Me | 3-Cl,4-Me-phenyl | |
| 1.163 | Me | Me | Me | 4-Cl,2-Me-phenyl | |
| 1.164 | Me | H | Me | 4-Cl,3-Me-phenyl | |
| 1.165 | Me | H | Me | 5-Cl,2-Me-phenyl | |
| 1.166 | Me | H | Me | 4-Cl,3-NO$_2$-phenyl | |
| 1.167 | Me | H | Me | 5-Indanyl | |
| 1.168 | Me | H | Me | 3,5-Dinitrophenyl | |
| 1.169 | Me | Me | Me | 2-Nitrophenyl | |
| 1.170 | Me | Me | Me | 3-Nitrophenyl | |
| 1.171 | Me | Me | Me | 4-Nitrophenyl | |
| 1.172 | Me | H | Me | 2-Ethylphenyl | |
| 1.173 | Me | H | Me | 3-Ethylphenyl | |
| 1.174 | Me | H | Me | 4-Ethylphenyl | |
| 1.175 | Me | H | Me | 4-Ethylphenyl | |
| 1.176 | Me | Me | Me | 3-Ethoxyphenyl | |
| 1.177 | Me | H | Me | 4-Ethoxyphenyl | |
| 1.178 | Me | Me | Me | 3-F,4-CH$_3$-phenyl | |
| 1.179 | Me | Me | Me | 4-F,3-NO$_2$-phenyl | |
| 1.180 | Me | H | Me | 4-Cl,3-CF$_3$-phenyl | |
| 1.181 | Me | Me | Et | 3-Hydroxyphenyl | |
| 1.182 | Me | Me | Me | 4-Hydroxyphenyl | |
| 1.183 | Me | Me | Me | 3-Hydroxy-4-methoxyphenyl | |
| 1.184 | Me | Me | Me | 4-Hydroxy-3-methylphenyl | |
| 1.185 | Me | Me | Me | 4-Hydroxy-3-nitrophenyl | |

TABLE 1-continued

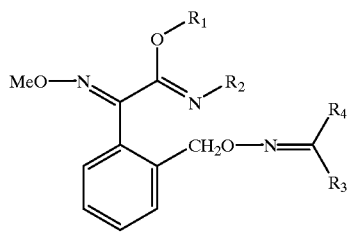

[Rhodano = thiocyano]

| | | | | |
|---|---|---|---|---|
| 1.186 | Me | H | Me | 4-Isopropylphenyl |
| 1.187 | Me | H | Me | 3-Iodophenyl |
| 1.188 | Me | H | Me | 4-Iodophenyl |
| 1.189 | Me | H | Me | 3-Mercaptophenyl |
| 1.190 | Me | H | Me | 4-Mercaptophenyl |
| 1.191 | Me | H | Me | 2-$NH_2C(S)$-phenyl |
| 1.192 | Me | H | Me | 3-$NH_2C(S)$-phenyl |
| 1.193 | Me | H | Me | 4-$NH_2C(S)$-phenyl |
| 1.194 | Me | H | Me | 3-Methylmercaptophenyl |
| 1.195 | Me | Me | Me | 4-Methylmercaptophenyl |
| 1.196 | Me | H | Me | 2-Methylthio-5-$CF_3$-phenyl |
| 1.197 | Me | Me | Me | 4-$CH_3$,3-$NO_2$-phenyl |
| 1.198 | Me | Me | Me | 4-$CH_3$,2-$NO_2$-phenyl |
| 1.199 | Me | Me | Me | 2-$CH_3$,4-$NO_2$-phenyl |
| 1.200 | Me | Me | Me | 2-$CH_3$,5-$NO_2$-phenyl |
| 1.201 | Me | Me | Me | 4-Methoxy,3-$NO_2$-phenyl |
| 1.202 | Me | Me | Me | 4-(4-Morpholino)phenyl |
| 1.203 | Me | H | Me | 3-Phenoxyphenyl |
| 1.204 | Me | Me | Me | 4-Phenoxyphenyl |
| 1.205 | Me | H | Me | 4-Propylphenyl |
| 1.206 | Me | Me | Me | 3-Methanesulfinylmethyl-4-MeO-phenyl |
| 1.207 | Me | H | Me | 4-Sulfamoylphenyl |
| 1.208 | Me | Me | Me | 4-MeO,3-$CH_3SCH_2$-phenyl |
| 1.209 | Me | Me | Me | 3-Trifluoromethylsulfonyl-phenyl |
| 1.210 | Me | H | Me | 3-Rhodanophenyl |
| 1.211 | Me | H | Me | 4-Rhodanophenyl |
| 1.212 | Me | H | Me | 3-Rhodanomethylphenyl |
| 1.213 | Me | H | Me | 4-Rhodanomethylphenyl |
| 1.214 | Me | H | Me | 3-Prop-1-en-3-yloxyphenyl |
| 1.215 | Me | H | Me | 3-Prop-1-yn-3-yloxyphenyl |
| 1.216 | Me | H | Me | 2-Cyclopropylmethoxyphenyl |
| 1.217 | Me | Me | Me | 2,3,4,5-Tetrafluorophenyl |
| 1.218 | Me | H | Me | 2,3,5,6-Tetrafluorophenyl |
| 1.219 | Me | H | Me | 2,3,5-Trimethoxyphenyl |
| 1.220 | Me | H | Me | 3,4,5-Trimethoxyphenyl |
| 1.221 | Me | H | Me | 5,6,7,8-Tetrahydro-1-naphthyl |
| 1.222 | Me | Me | Me | 2,3-Dihydrobenzofur-5-yl |
| 1.223 | Me | H | Me | 2,3-Dihydrobenzofur-6-yl |
| 1.224 | Me | Me | Me | 7-OMe,2,3-Dihydrobenzofur-5-yl |
| 1.225 | Me | H | Me | 3-Trimethylsilylphenyl |
| 1.226 | Me | H | $CF_3$ | 3-Trimethylsillylphenyl |
| 1.227 | Me | H | Me | Benzyl |
| 1.228 | Me | H | Me | 3-$CF_3$-benzyl |
| 1.229 | Me | Me | Me | 4-Chlorobenzyl |
| 1.230 | Me | H | Me | 3-$CF_3$,4-Chlorobenzyl |
| 1.231 | Me | H | Me | Phenoxymethyl |
| 1.232 | Me | Me | Me | 3-Chlorophenoxymethyl |
| 1.233 | Me | H | Me | 3-$CF_3$-phenoxymethyl |
| 1.234 | Me | H | Me | 2-Methoxy-5-benzodioxolyl |
| 1.235 | Me | Me | Me | 2-Methyl-5-benzodioxolyl |
| 1.236 | Me | H | Me | 2-Phenyl-5-benzodioxolyl |
| 1.237 | Me | H | Me | 3-Methoxycarbonylphenyl |
| 1.238 | Me | H | Me | 4-Methoxycarbonylphenyl |
| 1.239 | Me | H | Me | 3-Methoximinomethylphenyl |
| 1.240 | Me | Me | Me | 3-Ethoximinomethylphenyl |
| 1.241 | Me | Me | Me | 4-Methoximinomethylphenyl |
| 1.242 | Me | H | Me | 2-Pyrazinyl |
| 1.243 | Me | H | Me | 3,5-Dimethyl-pyrazin-2-yl |
| 1.244 | Me | H | Me | 3-Ethoxy-pyrazin-2-yl |
| 1.245 | Me | Me | Me | 5-$CONHCH_3$-pyrazin-2-yl |
| 1.246 | Me | H | Me | 2-Pyrimidinyl |
| 1.247 | Me | H | Me | 4-Chloropyrimidin-2-yl |

TABLE 1-continued

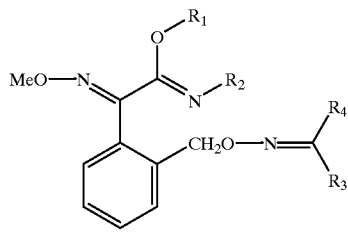

[Rhodano = thiocyano]

| No. | R1 | R2 | R3 | R4 |
|---|---|---|---|---|
| 1.248 | Me | H | Me | 4-Ethoxypyrimidin-2-yl |
| 1.249 | Me | Me | Me | 4-Methoxypyrimidin-2-yl |
| 1.250 | Me | H | Me | 4-(2,2,2-Trifluoroethoxy)-pyrimidin-2-yl |
| 1.251 | Me | H | Me | 2-SCH₃-pyrimidin-4-yl |
| 1.252 | Me | H | Me | 4-Isopropoxypyrimidin-2-yl |
| 1.253 | Me | H | Me | 4,6-Dimethylpyrimidin-2-yl |
| 1.254 | Me | H | Me | 4-Me,6-Cyclopropylpyrimidin-2-yl |
| 1.255 | Me | Me | Me | 4,6-Diethoxypyrimidin-2-yl |
| 1.256 | Me | Me | Me | 4-Me,6-OMe-pyrimidin-2-yl |
| 1.257 | Me | Me | Me | 4-Me,6-CF₃-pyrimidin-2-yl |
| 1.258 | Me | H | Me | 2-Pyridyl |
| 1.259 | Me | H | H | 2-Pyridyl |
| 1.260 | Me | Me | Me | 2-Pyridyl |
| 1.261 | Me | H | Me | 3-Pyridyl |
| 1.262 | Me | H | cyclopropyl | 4-Pyridyl |
| 1.263 | Me | Me | Me | 2,6-Dichloro-4-pyridyl |
| 1.264 | Me | H | Me | 2-Chloro-4-pyridyl |
| 1.265 | Me | H | Me | 2-Quinolinyl |
| 1.266 | Me | H | Me | 6-Quinolinyl |
| 1.267 | Me | Me | Me | 6-Quinolinyl |
| 1.268 | Me | H | Me | 7-Quinolinyl |
| 1.269 | Me | Me | Me | 7-Quinolinyl |
| 1.270 | Me | H | Me | 5-Isoquinolinyl |
| 1.271 | Me | H | Me | 2-Benzimidazolyl |
| 1.272 | Me | H | Me | 3,4-Benzocoumarin-6-yl |
| 1.273 | Me | Me | Me | 2-Thienyl |
| 1.274 | Me | Me | Me | 3-Methylbenzo(b)thien-2-yl |
| 1.275 | Me | H | Me | 5-Chlorothien-2-yl |
| 1.276 | Me | Me | Me | 5-Bromothien-2-yl |
| 1.277 | Me | Me | Me | 2-Methoxycarbonyl-3-thienyl |
| 1.278 | Me | Me | Me | 2-Furyl |
| 1.279 | Me | H | Me | Benzo[b]fur-2-yl |
| 1.280 | Me | Me | Me | 1-Methylpyrrol-2-yl |
| 1.281 | Me | Me | Me | 4-Methylthien-2-yl |
| 1.282 | Me | Me | Me | 5-Methylfur-2-yl |
| 1.283 | Me | H | Me | 6-Bromo-2-pyridyl |
| 1.284 | Me | H | Me | 4-Trifluoromethyl-2-pyridyl |
| 1.285 | Me | Me | Me | 4-Ethoxypyrimidin-2-yl |
| 1.286 | Me | Me | Me | 5-Chlor-2-pyridyl |
| 1.287 | Me | Me | Me | 5-Bromo-2-pyridyl |
| 1.288 | Me | Me | Me | 6-Trifluoromethyl-2-pyridyl |
| 1.289 | Me | H | Me | 6-Quinoxalinyl |
| 1.290 | Me | Me | Me | 6-Quinoxalinyl |
| 1.291 | Me | H | Me | 2-Quinoxalinyl |
| 1.292 | Me | H | Me | 6-Chloro-2-quinoxalinyl |
| 1.293 | Me | Me | Me | 2-Thiazolyl |
| 1.294 | Me | H | Me | 5-Trifluoromethyl-2-pyridyl |
| 1.295 | Me | H | Me | 2,1,3-Benzothiadiazol-5-yl |
| 1.296 | Me | H | Me | 2,1,3-Benzoxadiazol-5-yl |
| 1.297 | Me | Me | Me | 4-CN-2-pyridyl |
| 1.298 | Me | Me | Me | 5-Bromo-3-pyridyl |
| 1.299 | Me | Me | Me | 6-Methyl-3-pyridyl |
| 1.300 | Me | Me | Me | 1-Morpholinyl |
| 1.301 | Me | Me | Me | 1-(2,6-Dimethylmorpholinyl) |
| 1.302 | Me | H | Me | 1-(2-Methylmorpholinyl) |
| 1.303 | Me | H | Me | 1-Piperidinyl |
| 1.304 | Me | Me | Me | 1-Piperazinyl |
| 1.305 | Me | Me | Me | Methyl |

TABLE 1-continued

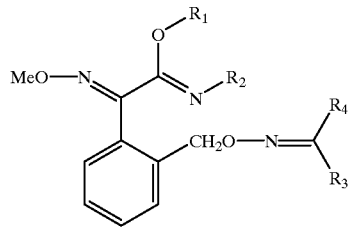

[Rhodano = thiocyano]

| Ex. No. | R₁ | R₂ | R₃ | R₄ | Physical data |
|---|---|---|---|---|---|
| 1.306 | Me | H | Me | Ethyl | |
| 1.307 | Me | H | Me | Propyl | |
| 1.308 | Me | H | Me | Isopropyl | |
| 1.309 | Me | Me | Me | Cyclopropyl | |
| 1.310 | Me | H |  | Cyclopropyl | |
| 1.311 | Me | H | Me | Ethoxy | |
| 1.312 | Me | Me | Me | Methylthio | |
| 1.313 | Me | H | CN | 2-Methoxyprop-2-yl | |
| 1.314 | Me | Me | CN | 2-n-Butoxyprop-2-yl | |
| 1.315 | Me | H | CN | 2-Methylthioprop-2-yl | |
| 1.316 | Me | Me | CN | Isopropyl | |
| 1.317 | Me | Me | CN | Cyclopropyl | |
| 1.318 | Me | H | CN | Phenyl | |
| 1.319 | Me | Me | CN | 2-n-Propoxyprop-2-yl | |
| 1.320 | Et | Me | CH₃S | 4-Chlorophenyl | oil; 433(2), 116 |
| 1.321 | Me | H | Me | 3-Trifluoromethoxy-phenyl | oil; 423(10), 116 |
| 1.322 | Et | Me | CH₃S | 3,4-Methylenedioxy-phenyl | oil; 443(12), 58 |
| 1.323 | Et | H | CH₃O | 3-Trifluoromethyl-phenyl | oil; 437(2), 116 |
| 1.324 | Et | Me | CH₃O | 3-Trifluoromethyl-phenyl | oil; 451(1), 58 |
| 1.325 | Me | Me | CH₃S | 4-Chlorophenyl | oil; 419(2.5), 72 |
| 1.326 | Et | Me |  | 4-Chorophenyl | 396 M-OMe(2), 116 |
| 1.327 | Et | H |  | 4-Chlorophenyl | 413(2); 116 |
| 1.328 | Et | H | Me | 3-Fluoro-4-methoxy-phenyl | 401(28); 116 |
| 1.329 | Me | Me | Me | 3-Fluoro-4-methoxy-phenyl | 401(7), 72 |
| 1.330 | Et | Me | Me | 3-Fluoro-4-methoxy-phenyl | 415(8), 116 |
| 1.331 | Et | H | Me | 4-Chlorophenyl | 387(18), 116 |
| 1.332 | Me | COMe | Me | 4-Chlorophenyl | 415(5.4), 43 |

| Ex. No. | R₁ | R₂ | N=C(R₃)R₄ | Physical data |
|---|---|---|---|---|
| 1.333 | Me | H | 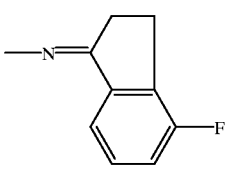 | |

TABLE 1-continued
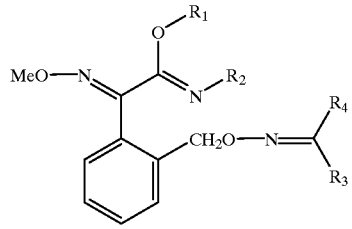
[Rhodano = thiocyano]
| | | | |
|---|---|---|---|
| 1.334 | Me | H | 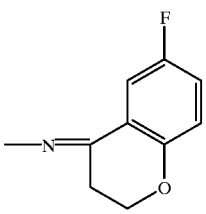 |
| 1.335 | Me | Me | 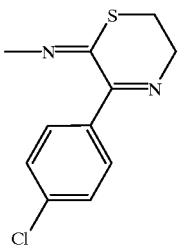 |
| 1.336 | Me | H | 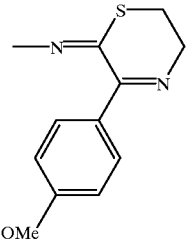 |
| 1.337 | Me | H | 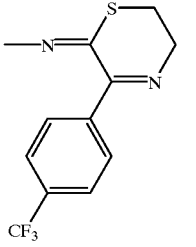 |
| 1.338 | Me | Me | 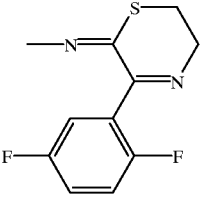 |

TABLE 1-continued

[Rhodano = thiocyano]

| | | | |
|---|---|---|---|
| 1.339 | Me | H | (2-isopropyl-5,6-dihydro-4H-1,3-thiazin-2-yl)imino |
| 1.340 | Me | Me | (2-(benzo[1,3]dioxol-5-yl)-5,6-dihydro-4H-1,3-thiazin-2-yl)imino |
| 1.341 | Me | H | (2-(4-phenoxyphenyl)-5,6-dihydro-4H-1,3-thiazin-2-yl)imino |
| 1.342 | Me | H | (2-(4-fluorophenyl)-5,6-dihydro-4H-1,3-thiazin-2-yl)imino |

TABLE 2

[Structure: central compound with MeO—N= and S—R₁, =N—R₂, connected to phenyl ring with ortho CH₂O—N=C(R₃)(R₄) substituent]

| Ex. No. | R₁ | R₂ | R₃ | R₄ | Physical data MS: molecular peak (%), base peak |
|---|---|---|---|---|---|
| 2.1 | Me | Me | Me | Phenyl | |
| 2.2 | Me | Me | H | 2-Fluorophenyl | |
| 2.3 | Me | Me | H | 3-Fluorophenyl | |
| 2.4 | Me | Me | Me | 4-Fluorophenyl | |
| 2.5 | Me | Me | cyclopropyl | 4-Fluorophenyl | |
| 2.6 | Me | Me | H | 2-Chlorophenyl | |
| 2.7 | Me | Me | H | 3-Chlorophenyl | |
| 2.8 | Me | Me | Me | Et | 3-Chlorophenyl |
| 2.9 | Me | Me | H | Me | 4-Chlorophenyl |
| 2.10 | Me | Me | Me | 4-Chlorophenyl | m.p. 102–103° C. |
| 2.11 | Me | H | cyclopropyl | 4-Chlorophenyl | |
| 2.12 | Me | Me | cyclopropyl | 4-Chlorophenyl | 430 (0.5), 178 |
| 2.13 | Me | Me | SCH₃ | 4-Chlorophenyl | 435 (0.1), 184 |
| 2.14 | Me | Me | OMe | 4-Chlorophenyl | |
| 2.15 | Me | Me | H | OMe | 4-Chlorophenyl |
| 2.16 | Me | Me | CH₂OCH₃ | 4-Chlorophenyl | |
| 2.17 | Me | Me | H | CF₃ | 4-Chlorophenyl |
| 2.18 | Me | Me | H | CN | 4-Chlorophenyl |
| 2.19 | Me | Me | H | Et | 4-Chlorophenyl |
| 2.20 | Me | Me | H | Me | 2-Bromophenyl |
| 2.21 | Et | Me | Me | 3-Bromophenyl | |
| 2.22 | Me | Me | H | Me | 4-Bromophenyl |
| 2.23 | Me | Me | H | Me | 2,4-Difluorophenyl |
| 2.24 | Me | Me | H | Me | 2,3-Difluorophenyl |
| 2.25 | Me | Me | Me | Me | 3,4-Difluorophenyl |
| 2.26 | Me | Me | H | Me | 2,5-Difluorophenyl |
| 2.27 | Me | Me | Me | Me | 3,5-Difluorophenyl |
| 2.28 | Me | Me | Me | Me | 3,4-Dichlorophenyl |
| 2.29 | Me | Me | Me | Me | 3,5-Dichlorophenyl |
| 2.30 | Me | Me | H | Me | 3-Cl, 4-F-phenyl |
| 2.31 | Me | Me | Me | Me | 2-Naphthyl |
| 2.32 | Me | Me | cyclopropyl | 2-Naphthyl | |
| 2.33 | Me | Me | H | Me | 2-Methylphenyl |
| 2.34 | Me | Me | Me | Me | 3-Methylphenyl |
| 2.35 | Me | Me | Me | Me | 4-Methylphenyl |
| 2.36 | Me | Me | Me | Me | 3-Methoxyphenyl |
| 2.37 | Me | Me | cyclopropyl | 3-Methoxyphenyl | |
| 2.38 | Me | Me | H | Me | 3,4-Methylenedioxyphenyl |
| 2.39 | Me | Me | Me | Me | 3,4-Methylenedioxyphenyl |
| 2.40 | Me | H | cyclopropyl | 3,4-Methylenedioxyphenyl | |

TABLE 2-continued

| | | | | | |
|---|---|---|---|---|---|
| 2.41 | Me | Me |  | 3,4-Methylenedioxyphenyl | |
| 2.42 | Me | H | SCH₃ | 3,4-Methylenedioxyphenyl | |
| 2.43 | Me | H | OCH₃ | 3,4-Methylenedioxyphenyl | |
| 2.44 | Me | Me | Me | 3,4-Ethylenedioxyphenyl | |
| 2.45 | Me | H |  | 3,4-Ethylenedioxyphenyl | |
| 2.46 | Me | H | Me | 2,2-Difluoro-5-benzodioxolyl | |
| 2.47 | Me | H | Et | 2,2-Difluoro-5-benzodioxolyl | |
| 2.48 | Me | H | Me | 3-Difluoromethoxyphenyl | |
| 2.49 | Me | Me | Me | 3-Difluoromethoxyphenyl | |
| 2.50 | Me | H | Me | 3-(2,2,2-Trifluoroethoxy)phenyl | |
| 2.51 | Me | H | Me | 3-Trifluoromethoxyphenyl | |
| 2.52 | Et | H | Me | 3-Trifluoromethoxyphenyl | |
| 2.53 | Me | Me | Me | 3-Trifluoromethoxyphenyl | |
| 2.54 | Et | Me | Me | 3-Trifluoromethoxyphenyl | |
| 2.55 | Me | Me | Me | 2-Trifluoromethylphenyl | |
| 2.56 | Me | H | Me | 3-Trifluoromethylphenyl | |
| 2.57 | Me | Me | Me | 3-Trifluoromethylphenyl | 437 (1), 186 |
| 2.58 | Me | Me |  | 3-Trifluoromethylphenyl | |
| 2.59 | Me | Me | CN | 3-Trifluoromethylphenyl | |
| 2.60 | Me | H | OMe | 3-Trifluoromethylphenyl | |
| 2.61 | Me | Me | SMe | 3-Trifluoromethylphenyl | |
| 2.62 | Me | OH | Me | 3-Trifluoromethylphenyl | |
| 2.63 | Me | OMe | Me | 3-Trifluoromethylphenyl | |
| 2.64 | Me | H | Me | 3,5-Bis(trifluoromethyl)phenyl | |
| 2.65 | Me | Me | Me | 4-F, 3-CF₃-phenyl | |
| 2.66 | Et | H | Me | 2-Cyanophenyl | |
| 2.67 | Me | H | Me | 3-Cyanophenyl | |
| 2.68 | Me | Me | Me | 3-Cyanomethoxyphenyl | |
| 2.69 | Me | Me | Me | 3-F, 5-CF₃-phenyl | |
| 2.70 | Me | H | Me | 4-Cl, 3-CH₃-phenyl | |
| 2.71 | Me | H | Me | 4-Ethylphenyl | |
| 2.72 | Me | H | Me | 2-SCH₃, 5-CF₃-phenyl | |
| 2.73 | Me | Me | Me | 4-OCH₃, 3-NO₂-phenyl | |
| 2.74 | Me | H | Me | 3-Phenoxyphenyl | |
| 2.75 | Me | Me | Me | 4-Phenoxyphenyl | |
| 2.76 | Me | Me | Me | 3-CH₂SOCH₃, 4-OCH₃-phenyl | |
| 2.77 | Me | Me | Me | 3-CH₂SCH₂, 4-OCH₃-phenyl | |
| 2.78 | Me | H | Me | 3-Prop-1-en-3-yloxyphenyl | |
| 2.79 | Me | H | Me | 3-Prop-1-yn-3-yloxyphenyl | |
| 2.80 | Me | H | Me | 3-Cyclopropylmethoxyphenyl | |
| 2.81 | Me | Me | Me | 2,3-Dihydrobenzofur-5-yl | |
| 2.82 | Me | H | Me | 3-CF₃, 4-Chlorobenzyl | |
| 2.83 | Me | H | Me | 3-CF₃-phenoxymethyl | |
| 2.84 | Me | H | Me | 2-Methoxy-5-benzodioxolyl | |
| 2.85 | Me | H | Me | 2-Pyridyl | |
| 2.86 | Me | Me | Me | 7-Quinolinyl | |
| 2.87 | Me | H | Me | 6-Quinolinyl | |
| 2.88 | Me | Me | Me | 2-Thienyl | |
| 2.89 | Me | Me | Me | 3-Methylbenzo(b)thien-2-yl | |
| 2.90 | Me | H | Me | 5-Chlorothien-2-yl | |
| 2.91 | Me | Me | Me | 5-Bromothien-2-yl | |
| 2.92 | Me | Me | Me | 2-Furyl | |
| 2.93 | Me | H | Me | Benzo[b]fur-2-yl | |
| 2.94 | Me | Me | Me | 1-Methylpyrrol-2-yl | |
| 2.95 | Me | H | Me | 6-Bromo-2-pyridyl | |
| 2.96 | Me | H | Me | 4-CF₃-2-pyridyl | |
| 2.97 | Me | H | Me | 6-Quinoxolinyl | |
| 2.98 | Me | Me | Me | 6-Quinoxolinyl | |
| 2.99 | Me | Me | Me | 2-Thiazolyl | |
| 2.100 | Me | Me | Me | 1-(2,6-Dimethylmorpholinyl) | |
| 2.101 | Et | Me | Me | 3-Trifluoromethylphenyl | 451 (1), 186 |
| 2.102 | CH₂=CH—CH₂ | Me | Me | 4-Chlorophenyl | |
| 2.103 | CH₂=C(Me)—CH₂ | Me | Me | 3-Fluoro-4-methoxyphenyl | |
| 2.104 | 4-Chlorobenzyl | Me | Me | 3-Fluoro-4-methoxyphenyl | |
| 2.105 | Cyclopropylmethyl | Me | Me | 3-Fluoro-4-methoxyphenyl | |
| 2.106 | 4-Methoxybenzyl | Me | Me | 3-Fluoro-4-methoxyphenyl | |

TABLE 2-continued

| Ex. No. | R₁ | R₂ | | 3-position substituent | MS data |
|---|---|---|---|---|---|
| 2.107 | CH₃—O—CH₂ | Me | Me | 3-Fluoro-4-methoxyphenyl | |
| 2.108 | FCH₂—CH₂ | Me | Me | 4-Chlorophenyl | |
| 2.109 | F₃C—CH₂ | Me | Me | 4-Chlorophenyl | |
| 2.110 | n-propyl | Me | Me | 4-Chlorophenyl | |
| 2.111 | NC—CH₂ | Me | Me | 4-Chlorophenyl | |
| 2.112 | CH₂=CH—CH₂ | Me | Me | 3-Chloro-4-methoxyphenyl | |
| 2.113 | Et | Me | Me | 3-Chloro-4-methoxyphenyl | |
| 2.114 | Me | OMe | Me | 4-Chlorophenyl | 419 (0.5), 267 |
| 2.115 | CH₂=CH—CH₂ | Me |  | 4-Chlorophenyl | 456 (1), 41 |
| 2.116 | Et | Me | Me | 3-Fluoro-4-methoxyphenyl | 431 (0.5), 166 |
| 2.117 | CH₂=CH—CH₂ | Me | Me | 3-Fluoro-4-methoxyphenyl | 443 (1.5), 166 |
| 2.118 | Benzyl | Me | Me | 3-Fluoro-4-methoxyphenyl | 462 M-OMe (8), 166 |
| 2.119 | Et | Me | Me | 4-Chlorophenyl | 417 (1.4), 152 |
| 2.120 | 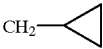CH₂— | Me | Me | 4-Chlorophenyl | 443 (0.7), 152 |
| 2.121 | CH₂—C≡CH | Me | Me | 4-Chlorophenyl | 427 (0.3), 152 |
| 2.122 | Isopropyl | Me | Me | 4-Chlorophenyl | 431 (1.1), 152 |
| 2.123 | CH₃\|CH-COOisobutyl | Me | Me | 4-Chlorophenyl | 517 (0.5), 152 |
| 2.124 | CH₂—COOMe | Me | Me | 4-Chlorophenyl | 461 (0.5), 152 |

| Ex. No. | R₁ | R₂ | N=C(R₃)R₄ |
|---|---|---|---|
| 2.125 | Me | H | 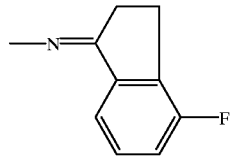 |
| 2.126 | Me | H | 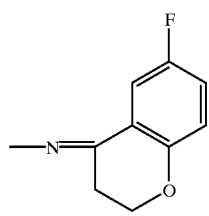 |
| 2.127 | Me | Me | 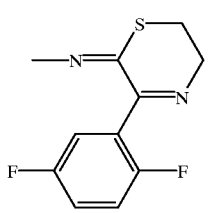 |
| 2.128 | Me | Me | 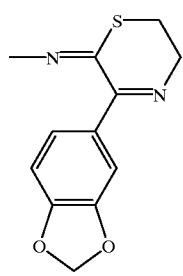 |

TABLE 2-continued

| | | | |
|---|---|---|---|
| 2.129 | Me | H | [structure: 6-membered ring with S and N, N=C linked to 4-methoxyphenyl, N-Me substituent] |

TABLE 3

[Structure: central backbone with MeO-N= group and R_6-N(R_1) group on one carbon, =N-R_2 on adjacent carbon, attached to ortho-substituted phenyl ring bearing CH_2-O-N=C(R_3)(R_4)]

| Ex. No. | $R_1$ | $R_6$ | $R_2$ | $R_3$ | $R_4$ | Physical data MS: molecular peak (%), base peak |
|---|---|---|---|---|---|---|
| 3.1 | Me | H | Me | Me | Phenyl | |
| 3.2 | Me | Me | Me | Me | 2-Fluorophenyl | |
| 3.3 | Me | H | Me | Me | 3-Fluorophenyl | |
| 3.4 | Me | H | H | Me | 4-Fluorophenyl | |
| 3.5 | Me | H | Me | cyclopropyl | 4-Fluorophenyl | |
| 3.6 | Me | Me | H | Me | 2-Chlorophenyl | |
| 3.7 | Me | Me | Me | Me | 3-Chlorophenyl | |
| 3.8 | Me | H | Me | Et | 3-Chlorophenyl | |
| 3.9 | Me | H | H | Me | 4-Chlorophenyl | |
| 3.10 | Me | Me | H | Me | 4-Chlorophenyl | |
| 3.11 | Me | H | Me | Me | 4-Chlorophenyl | 386 (3.2), 71 |
| 3.12 | Me | Me | Me | Me | 4-Chlorophenyl | |
| 3.13 | Me | H | Me | cyclopropyl | 4-Chlorophenyl | |
| 3.14 | Me | Me | Me | cyclopropyl | 4-Chlorophenyl | |
| 3.15 | cyclopropyl | H | Me | OMe | 4-Chlorophenyl | |
| 3.16 | Me | H | Me | SMe | 4-Chlorophenyl | |
| 3.17 | Et | H | Me | CN | 4-Chlorophenyl | |
| 3.18 | CH_2=CH—CH_2 | H | Me | CF_3 | 4-Chlorophenyl | |
| 3.19 | Me | Me | Me | Et | 4-Chlorophenyl | |
| 3.20 | iso-Prop | H | Me | Me | 2-Bromophenyl | |
| 3.21 | Me | H | Me | Me | 3-Bromophenyl | |
| 3.22 | Me | H | Me | Me | 4-Bromophenyl | |
| 3.23 | Me | H | H | Me | 2,4-Difluorophenyl | |
| 3.24 | Me | H | H | Me | 2,3-Difluorophenyl | |
| 3.25 | Me | H | Me | Me | 3,4-Difluorophenyl | |
| 3.26 | Me | Me | H | Me | 2,5-Difluorophenyl | |
| 3.27 | Me | H | Me | Me | 3,5-Difluorophenyl | |
| 3.28 | Me | H | Me | Me | 3,4-Dichlorophenyl | |
| 3.29 | Me | H | Me | Me | 3,5-Dichlorophenyl | |
| 3.30 | Me | Me | H | Me | 3-Cl, 4-F-phenyl | |

TABLE 3-continued

| | | | | | |
|---|---|---|---|---|---|
| 3.31 | Me | H | Me | Me | 2-Naphthyl |
| 3.32 | Me | Me | Me |  | 2-Naphthyl |
| 3.33 | Me | Me | H | Me | 2-Methylphenyl |
| 3.34 | Me | H | Me | Me | 3-Methylphenyl |
| 3.35 | Me | H | Me | Me | 4-Methylphenyl |
| 3.36 | Me | H | Me | Me | 3-Methoxyphenyl |
| 3.37 | Me | | H | Me |  | 3-Methoxyphenyl |
| 3.38 | Me | Me | H | Me | 3,4-Methylenedioxyphenyl |
| 3.39 | Me | H | Me | Me | 3,4-Methylenedioxyphenyl |
| 3.40 | Me | Me | H |  | 3,4-Methylenedioxyphenyl |
| 3.41 | Me | H | Me |  | 3,4-Methylenedioxyphenyl |
| 3.42 | Me | Me | H | SCH$_3$ | 3,4-Methylenedioxyphenyl |
| 3.43 | Me | Me | H | OCH$_3$ | 3,4-Methylenedioxyphenyl |
| 3.44 | Me | H | Me | Me | 3,4-Ethylenedioxyphenyl |
| 3.45 | Me | Me | H |  | 3,4-Ethylenedioxyphenyl |
| 3.46 | Me | Me | H | Me | 2,2-Difluoro-5-benzodioxolyl |
| 3.47 | Me | Me | H | Et | 2,2-Difluoro-5-benzodioxolyl |
| 3.48 | Me | Me | H | Me | 3-Difluoromethoxyphenyl |
| 3.49 | Me | H | Me | Me | 3-Difluoromethoxyphenyl |
| 3.50 | Me | Me | H | Me | 3-(2,2,2-Trifluoroethoxy)phenyl |
| 3.51 | Me | H | H | Me | 3-Trifluoromethoxyphenyl |
| 3.52 | Et | Me | H | Me | 3-Trifluoromethoxyphenyl |
| 3.53 | Me | H | Me | Me | 3-Trifluoromethoxyphenyl |
| 3.54 | Et | H | Me | Me | 3-Trifluoromethoxyphenyl |
| 3.55 | Me | H | Me | Me | 2-Trifluoromethylphenyl |
| 3.56 | Me | Me | H | Me | 3-Trifluoromethylphenyl |
| 3.57 | Me | H | Me | Me | 3-Trifluoromethylphenyl |
| 3.58 | Me | | H | Me |  | 3-Trifluoromethylphenyl |
| 3.59 | Me | H | Me | CN | 3-Trifluoromethylphenyl |
| 3.60 | Me | Me | H | OMe | 3-Trifluoromethylphenyl |
| 3.61 | Me | H | Me | SMe | 3-Trifluoromethylphenyl |
| 3.62 | Me | Me | OH | Me | 3-Trifluoromethylphenyl |
| 3.63 | Me | Me | OMe | Me | 3-Trifluoromethylphenyl |
| 3.64 | Me | Me | H | Me | 3,5-Bis(trifluromethyl)phenyl |
| 3.65 | Me | H | Me | Me | 4-F, 3-CF$_3$-phenyl |
| 3.66 | Et | H | H | Me | 2-Cyanophenyl |
| 3.67 | Me | Me | H | Me | 3-Cyanophenyl |
| 3.68 | Me | H | Me | Me | 3-Cyanomethoxyphenyl |
| 3.69 | Me | H | Me | Me | 3-F, 5-CF$_3$-phenyl |
| 3.70 | Me | Me | H | Me | 4-Cl, 3-CH$_3$-phenyl |
| 3.71 | Me | Me | H | Me | 4-Ethylphenyl |
| 3.72 | Me | Me | H | Me | 2-SCH$_3$, 5-CF$_3$-phenyl |
| 3.73 | Me | H | Me | Me | 4-OCH$_3$, 3-NO$_2$-phenyl |
| 3.74 | Me | H | H | Me | 3-Phenoxyphenyl |
| 3.75 | Me | H | Me | Me | 4-Phenoxyphenyl |
| 3.76 | Me | H | Me | Me | 3-CH$_2$SOCH$_3$, 4-OCH$_3$-phenyl |
| 3.77 | Me | H | Me | Me | 3-CH$_2$SCH$_3$, 4-OCH$_3$-phenyl |
| 3.78 | Me | H | H | Me | 3-Prop-1-en-3-yloxyphenyl |
| 3.79 | Me | H | H | Me | 3-Prop-1-yn-3-yloxyphenyl |
| 3.80 | Me | H | H | Me | 3-Cyclopropylmethoxyphenyl |
| 3.81 | Me | Me | Me | Me | 2,3-Dihydrobenzofur-5-yl |
| 3.82 | Me | H | H | Me | 3-CF$_3$, 4-Chlorobenzyl |
| 3.83 | Me | Me | H | Me | 3-CF$_3$-phenoxymethyl |
| 3.84 | Me | Me | H | Me | 2-OCH$_3$-5-benzodioxolyl |
| 3.85 | Me | H | H | Me | 2-Pyridyl |

TABLE 3-continued

| Ex. No. | R₁ | R₆ | | R₂ | N=C(R₃)₄ | |
|---|---|---|---|---|---|---|
| 3.86 | Me | H | Me | Me | 7-Quinolinyl | |
| 3.87 | Me | Me | H | Me | 6-Quinolinyl | |
| 3.88 | Me | Me | Me | Me | 2-Thienyl | |
| 3.89 | Me | H | Me | Me | 3-Methylbenzo[b]thien-2-yl | |
| 3.90 | Me | Me | H | Me | 5-Chlorothien-2-yl | |
| 3.91 | Me | H | Me | Me | 5-Bromothien-2-yl | |
| 3.92 | Me | Me | Me | Me | 2-Furyl | |
| 3.93 | Me | H | H | Me | Benzo[b]fur-2-yl | |
| 3.94 | Me | H | Me | Me | 1-Methylpyrrol-2-yl | |
| 3.95 | Me | H | H | Me | 6-Bromo-2-pyridyl | |
| 3.96 | Me | H | H | Me | 4-CF₃-2-pyridyl | |
| 3.97 | Me | H | H | Me | 6-Quinoxalinyl | |
| 3.98 | Me | Me | Me | Me | 6-Quinoxalinyl | |
| 3.99 | Me | H | Me | Me | 2-Thiazolyl | |
| 3.100 | Me | Me | Me | Me | 1-(2,6-Dimethylmorpholinyl) | |
| 3.101 | H | H | OMe | Me | 4-Chlorophenyl | m.p. 76–78° C. |
| 3.102 | Me | H | OMe | Me | 4-Chlorophenyl | 402 (2), 250 |
| 3.103 | H | H | H | Me | 4-Chlorophenyl | 358 (2), 43 |
| 3.104 | Me | H | OEt | Me | 4-Chlorophenyl | 416 (3.6), 264 |
| 3.105 | Me | H | OH | Me | 4-Chlorophenyl | m.p. 124–125° C. |
| 3.106 | H | H | OH | Me | 4-Chlorophenyl | 376 (9.3), 116 |
| 3.107 | H | H | NH₂ | Me | 4-Chlorophenyl | 373 (32), 221 |
| 3.108 | H | H | NHMe | Me | 4-Chlorophenyl | 387 (45), 235 |
| 3.109 | NHMe | H | Me | Me | 4-Chlorophenyl | 401 (10), 116 |
| 3.110 | COMe | Me | OEt | Me | 4-Chlorophenyl | 458 (0.5), 56 |

| Ex. No. | R₁ | R₆ | R₂ | N=C(R₃)₄ |
|---|---|---|---|---|
| 3.111 | Me | H | H | |
| 3.112 | Me | H | Me | |

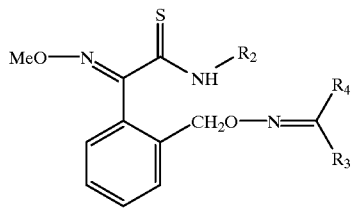

TABLE 4

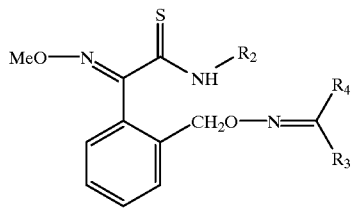

| Ex. No. | R₂ | R₃ | R₄ | Physical data MS: molecular peak %, base peak |
|---|---|---|---|---|
| 4.1 | Me | Me | Phenyl | |
| 4.2 | Me | H | 2-Fluorophenyl | |
| 4.3 | H | Me | 3-Fluorophenyl | |
| 4.4 | Me | Me | 4-Fluorophenyl | |

TABLE 4-continued

| | | | | |
|---|---|---|---|---|
| 4.5 | Me |  | 4-Fluorophenyl | |
| 4.6 | Me | H | 2-Chlorophenyl | |
| 4.7 | Me | Me | 3-Chlorophenyl | |
| 4.8 | Me | Et | 3-Chlorophenyl | |
| 4.9 | H | Me | 4-Chlorophenyl | |
| 4.10 | Me | Me | 4-Chlorophenyl | m.p. 88–89° C. |
| 4.11 | Me |  | 4-Chlorophenyl | 416 M + H(0.5), 74 |
| 4.12 | Me | SCH$_3$ | 4-Chlorophenyl | 388 M − SH(0.7), 237 |
| 4.13 | Me | OCH$_3$ | 4-Chlorophenyl | |
| 4.14 | Me | CH$_2$OCH$_3$ | 4-Chlorophenyl | |
| 4.15 | Me | CF$_3$ | 4-Chlorophenyl | |
| 4.16 | Me | CN | 4-Chlorophenyl | |
| 4.17 |  | Me | 4-Chlorophenyl | |
| 4.18 | Me | Me | 2-Bromophenyl | |
| 4.19 | Me | Me | 3-Bromophenyl | |
| 4.20 | Me | Me | 4-Bromophenyl | |
| 4.21 | Me | Me | 2,4-Difluorophenyl | |
| 4.22 | Me | Me | 2,3-Difluorophenyl | |
| 4.23 | Me | Me | 3,4-Difluorophenyl | |
| 4.24 | Me | Me | 2,5-Difluorophenyl | |
| 4.25 | Me | Me | 3,5-Difluorophenyl | |
| 4.26 | Me | Me | 3,4-Dichlorophenyl | |
| 4.27 | Me | Me | 3,5-Dichlorophenyl | |
| 4.28 | Me | Me | 3-Cl,4-F-phenyl | |
| 4.29 | Me | Me | 2-Naphthyl | |
| 4.30 | Me | Me | 2-Naphthyl | |
| 4.31 | Me | Me | 2-Methylphenyl | |
| 4.32 | Me | Me | 3-Methylphenyl | |
| 4.33 | Me | Me | 4-Methylphenyl | |
| 4.34 | Me | Me | 3-Methoxyphenyl | |
| 4.35 | Me | Me | 3-Methoxyphenyl | |
| 4.36 | Me | Me | 3,4-Methylenedioxyphenyl | |
| 4.37 | Me |  | 3,4-Methylenedioxyphenyl | |
| 4.38 | Me | SCH$_3$ | 3,4-Methylenedioxyphenyl | |
| 4.39 | Me | OCH$_3$ | 3,4-Methylenedioxyphenyl | |
| 4.40 | Me | CN | 3,4-Methylenedioxyphenyl | |
| 4.41 | Me | Me | 3,4-Ethylenedioxyphenyl | |
| 4.42 | Me |  | 3,4-Ethylenedioxyphenyl | |
| 4.43 | Me | Me | 2,2-Difluoro-5-benzodioxolyl | |
| 4.44 | Me | Et | 2,2-Difluoro-5-benzodioxolyl | |
| 4.45 | Me | Me | 3-Difluoromethoxyphenyl | |
| 4.46 | Me | Me | 3-(2,2,2-Trifluoroethoxy)-phenyl | |
| 4.47 | Me | Me | 3-Trifluoromethoxyphenyl | |
| 4.48 | Me | OMe | 3-Trifluoromethoxyphenyl | |
| 4.49 | Me | SMe | 3-Trifluoromethoxyphenyl | |
| 4.50 | Me | Me | 2-Trifluoromethylphenyl | |
| 4.51 | Me | Me | 3-Trifluoromethyl-phenyl | 424(0.1), 74 |
| 4.52 | Me |  | 3-Trifluoromethylphenyl | |
| 4.53 | Me | CN | 3-Trifluoromethylphenyl | |
| 4.54 | Me | OMe | 3-Trifluoromethylphenyl | |
| 4.55 | Me | SMe | 3-Trifluoromethylphenyl | |
| 4.56 | OMe | Me | 3-Trifluoromethylphenyl | |
| 4.57 | Me | Me | 3,5-Bis(trifluoromethyl)phenyl | |
| 4.58 | Me | Me | 4-F,3-CF$_3$-phenyl | |

TABLE 4-continued

| | | | | |
|---|---|---|---|---|
| 4.59 | Me | Me | 2-Cyanophenyl | |
| 4.60 | Me | Me | 3-Cyanophenyl | |
| 4.61 | Me | Me | 3-Cyanomethoxyphenyl | |
| 4.62 | OH | Me | 3-F,5-CF$_3$-phenyl | |
| 4.63 | Me | Me | 4-Cl,3-CH$_3$-phenyl | |
| 4.64 | Me | Me | 4-Ethylphenyl | |
| 4.65 | Me | Me | 2-SCH$_3$,5-CF$_3$-phenyl | |
| 4.66 | Et | Me | 4-OCH$_3$,3-NO$_2$-phenyl | |
| 4.67 | Me | Me | 3-Phenoxyphenyl | |
| 4.68 | Me | Me | 4-Phenoxyphenyl | |
| 4.69 | Me | Me | 3-CH$_2$SOCH$_3$,4-OCH$_3$-phenyl | |
| 4.70 | Me | Me | 3-CH$_2$SCH$_3$,4-OCH$_3$-phenyl | |
| 4.71 | Me | Me | 3-Prop-1-en-3-yloxyphenyl | |
| 4.72 | Me | Me | 3-Prop-1-yn-3-yloxyphenyl | |
| 4.73 | Me | Me | 3-Cyclopropylmethoxyphenyl | |
| 4.74 | Me | Me | 2,3-Dihydrobenzofur-5-yl | |
| 4.75 | Me | Me | 3-CF$_3$,4-Chlorobenzyl | |
| 4.76 | Me | Me | 3-CF$_3$-phenoxymethyl | |
| 4.77 | Me | Me | 2-Methoxy-5-benzodioxolyl | |
| 4.78 | Me | Me | 2-Pyridyl | |
| 4.79 | Me | Me | 6-Quinolinyl | |
| 4.80 | Me | Me | 7-Quinolinyl | |
| 4.81 | OMe | Me | 2-Thienyl | |
| 4.82 | Me | Me | 3-Methylbenzo[b]thien-2-yl | |
| 4.83 | CH$_2$—CH=CH$_2$ | Me | 5-Chlorothien-2-yl | |
| 4.84 | Me | Me | 5-Bromothien-2-yl | |
| 4.85 | Me | Me | 2-Furyl | |
| 4.86 | Me | Me | Benzo[b]fur-2-yl | |
| 4.87 | OH | Me | 1-Methylpyrrol-2-yl | |
| 4.88 | Cyclohexyl | Me | 6-Bromo-2-pyridyl | |
| 4.89 | Me | Me | 4-CF$_3$-2-pyridyl | |
| 4.90 | Me | Me | 6-Quinoxalinyl | |
| 4.91 | Me | Me | 2-Thiazolyl | |
| 4.92 | Me | Me | 1-(2,6-Dimethylmorpholinyl) | |
| 4.93 | Me | Me | 3-Fluoro-4-methoxy-phenyl | 404 M + H(0.5), 74 |

| Ex. No. | R$_2$ | N=C(R$_3$)R$_4$ |
|---|---|---|
| 4.94 | Me | (4-fluoro-2,3-dihydro-1H-inden-1-ylidene) |
| 4.95 | Me | (3-(4-methoxyphenyl)-5,6-dihydro-2H-1,4-thiazin-2-ylidene) |
| 4.96 | Me | (3-(1,3-benzodioxol-5-yl)-5,6-dihydro-2H-1,4-thiazin-2-ylidene) |

2. Formulation examples of active ingredients of the formula I (%=percent by weight)

2.1 Wettable powders

|  | a) | b) | c) |
|---|---|---|---|
| Active ingredient of Tables 1–4 | 25% | 50% | 75% |
| Sodium ligninsulfonate | 5% | 5% | — |
| Sodium lauryl sulfate | 3% | — | 5% |
| Soidum diisobutylnaphthalene sulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives and ground thoroughly in a suitable mill. This gives wettable powders which can be diluted with water to give suspensions of any desired concentration.

2.2. Emulsifiable concentrate

| Active ingredient of Tables 1–4 | 25% |
|---|---|
| Castor oil (36 mol of ethylene oxide)(alcohol-free) | 6% |
| Calcium dodecylbenzenesulfonate (alcohol free) | 4% |
| Cyclohexanone | 5% |
| Soybean oil (39 mol of ethylene oxide) | 5% |
| Triethanol amine | 5% |
| Xylene/toluene mixture | 50% |

Emulsions of any desired dilution can be prepared from this concentrate by diluting it with water.

2.3. Dusts

|  | a) | b) |
|---|---|---|
| Active ingredient of Tables 1–4 | 5% | 8% |
| Talc | 95% | — |
| Kaolin | — | 92% |

Ready-to-use dusts are obtained by mixing the active ingredient with the carrier and grinding the mixture on a suitable mill.

2.4 Wettable powder

|  | d) |
|---|---|
| Active ingredient of Tables 1–4 | 25% |
| Sodium ligninsulfonate | 5% |
| Kieselguhr | 25% |
| Sodiumcarbonate | 5% |
| Disodium 1-benzyl-2-heptadecylbenzimidazol-X,X'-disulfonic acid (incl. 15–30% Na$_2$SO$_4$) | 5% |
| Champagne chalk | 35% |

The active ingredient is mixed with the additives, and ground. This mixture fits for all kinds of foliar applications.

2.5. Coated granules

| Active ingredient of Tables 1–4 | 3% |
|---|---|
| Polyethylene glycol (MW 200) | 3% |
| Kaolin | 94% |

(MW = molecular weight)

In a mixer, the finely-ground active ingredient is applied uniformly to the kaolin which has been moistened with polyethylene glycol. In this manner, dust-free coated granules are obtained.

2.6. Suspension concentrate

| Active ingredient of Tables 1–4 | 40% |
|---|---|
| Ethylene glycol | 10% |
| Nonylphenol polyethylene glycol ether (15 mol of ethylene oxide) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely-ground active ingredient is mixed intimately with the additives. This gives a suspension concentrate from which suspensions of any desired dilution can be prepared by diluting it with water.

3. Biological Examples

In the Examples B-1 to B-12 which follow, active ingredients according to the invention exhibit good activities against attack by fungi.

EXAMPLE B-1

Activity Against *Phytophthora infestans* on Tomatoes a) Curative Activity

Tomato plants cv. "Roter Gnom" are grown for three weeks and then sprayed with a zoospore suspension of the fungus and incubated in a cabin at 18 to 20° and in a moisture-saturated atmosphere. The humidification is interrupted after 24 hours. After the plants have dried, they are sprayed with a mixture comprising the active ingredient, formulated as a wettable powder, at a concentration of 200 ppm. After the spraycoating has dried on, the plants are returned to the humid chamber for 4 days. Number and size of the typical lesions which have appeared after this period are used to assess the activity of the test substances.

b) Preventive-systemic Activity

The active ingredient, formulated as a wettable powder, is applied to the soil surface of 3-week-old tomato plants cv. "Roter Gnom" in pots, at a concentration of 60 ppm (based on the volume of soil). After a waiting period of 3 days, the underside of the plants' leaves is sprayed with a zoospore suspension of *Phytophthora infestans*. They were then kept for 5 days in a spray cabin at 18–20° C. under a moisture-saturated atmosphere. After this time, typical lesions are formed, whose number and size are used to assess the activity of the test substances.

While untreated, but infected control plants show an infestation of 100%, the active ingredients of the formula I of one of Tables 1, 2, 3 or 4 reduce infestation in both tests to 20% or below. Compounds Nos. 1.13; 1.14; 1.24; 1.86; 1.112; 1.116; 1.117; 1.160; 1.320–1.332; 2.10; 2.12; 2.13; 2.57; 2.101; 2.114–2.124; 3.11; 3.101–3.110; 4.10–4.12; 4.51; 4.93 and others exhibit a complete control (0–5% attack).

EXAMPLE B-2
Activity Against *Plasmopara viticola* (Bert. et Curt.) (Berl. et DeToni) on Grape Vines
a) Residual-preventive Activity Vine seedlings cv. "Chasselas" are grown in a greenhouse. 3 plants at the 10-leaf stage are sprayed with a mixture (200 ppm of active ingredient). After the spraycoating has dried on, the underside of the plants' leaves is infected uniformly with a spore suspension of the fungus. The plants are subsequently kept in a humid chamber for 8 days. After this time, pronounced disease symptoms appear on the control plants. Number and size of the infected areas on the treated plants are used to assess the activity of the test substances.
b) Curative Activity Vine seedlings cv. "Chasselas" are grown in the greenhouse and, at the 10-leaf stage, the underside of the leaves is infected with a spore suspension of Plasmopara viticola. After the plants have remained in a humid chamber for 24 hours, they are sprayed with a mixture comprising active ingredient (200 ppm of active ingredient). The plants are then kept in the humid chamber for another 7 days. After this time, the disease symptoms on the control plants show. Number and size of the infected areas on the treated plants are used to assess the activity of the test substances.

Compared with the control plants, the plants which were treated with active ingredients of the formula I show an infestation of 20% or less, in the majority of cases less than 10%.

EXAMPLE B-3
Activity Against *Pythium debaryanum* on Sugarbeet (Beta Vulgaris)
a) Activity After Soil Drench The fungus is grown on sterile oat kernels and added to a mixture of soil and sand. This infected soil is filled into flowerpots, and sugarbeet seeds are sown. Immediately after sowing, the test preparations formulated as wettable powders are poured over the soil in the form of an aqueous suspension (20 ppm of active ingredient based on the volume of soil). Hereupon, the plants are placed in a greenhouse at 20–24° C. for 2–3 weeks. The soil is constantly kept uniformly moist by lightly spraying on water. When the tests are evaluated, the emergence of the sugarbeet plants and the proportion of healthy and diseased plants is determined.
b) Activity After Seed-dressing The fungus is grown on sterile oat kernels and added to a mixture of soil and sand. This infected soil is filled into flowerpots, and sugarbeet seeds, which had been treated with the test preparations formulated as seed-dressing powders (1000 ppm of active ingredient based on the weight of the seeds) are sown. The pots together with the seeds were placed in a greenhouse at 20–24° C. for 2–3 weeks. The soil is kept uniformly moist by lightly spraying on water.

When the test is evaluated, the emergence of the sugarbeet plants and the proportion of healthy and diseased plants is determined.

After treatment with active ingredients of the formula I, more than 80% of the plants emerge and have a healthy appearance. In the control pots, plants emerge only occasionally and have an unhealthy appearance.

EXAMPLE B-4
Residual-protective Activity Against *Cercospora arachidicola* on Goundnuts Groundnut plants 10 to 15 cm in height are sprayed to drip point with an aqueous spray mixture (0.02% of active ingredient) and, 48 hours later, infected with a conidia suspension of the fungus. The plants are incubated for 72 hours at 21° and a high atmospheric humidity and subsequently placed in a greenhouse until the typical lesions occur. The activity of the active ingredient is assessed 12 days after infection on the basis of number and size of the lesions.

Active ingredients of the formula I cause a reduction in lesions to below approximately 10% of the leaf surface. In some cases, the disease is suppressed completely (infestation 0–5%).

EXAMPLE B-5
Activity Against *Puccinia Graminis* on Wheat
a) Residual-protective Activity 6 days after sowing, wheat plants are sprayed to drip point with an aqueous spray mixture (0.02% of active ingredient) and, 24 hours later, infected with an uredo spore suspension of the fungus. After an incubation time of 48 hours (conditions: 95 to 100 per cent relative atmospheric humidity at 20°), the plants are placed in a greenhouse at 22°. The development of the rust pustules is assessed 12 days after infection.
b) Systemic Activity 5 days after sowing, an aqueous spray mixture (0.006% of active ingredient based on the volume of soil) is poured in the vicinity of wheat plants. Care is taken that the spray mixture does not come into contact with aerial parts of the plants. 48 hours later, the plants are infected with a uredo spore suspension of the fungus. After an incubation time of 48 hours (conditions: 95 to 100 per cent relative atmospheric humidity at 20°), the plants are placed in a greenhouse at 22°. The development of the rust pustules is assessed 12 days after infection.

Compounds of the formula I cause a marked reduction of fungus infestation, in some cases down to 10–0 %. Examples are the compounds of H-1, H-2, H-4 as well as compounds Nos. 1.13; 1.14; 1.24; 1.86; 1.112; 1.116; 1.117; 1.160; 1.320–1.332; 2.10; 2.12; 2.13; 2.57; 2.101; 2.114–2.124; 3.11; 3.101–3.110; 4.10–4.12; 4.51; 4.93 and others.

EXAMPLE B-6
Activity Against *Pyricularia oryzae* in Rice
a) Residual-protective Activity Rice plants are grown for two weeks and then sprayed to drip point with an aqueous spray mixture (0.02% of active ingredient) and, 48 hours later, infected with a conidia suspension of the fungus. The fungus infestation is assessed 5 days after infection, over which a relative atmospheric humidity of 95 to 100 per cent and a temperature of 22° are maintained.
b) Systemic Activity An aqueous spray mixture (0.006% of active ingredient, based on the volume of soil) is poured in the vicinity of 2-week-old rice plants. Care is taken that the spray mixture does not come into contact with aerial parts of the plants. The pots are then filled with water to such an extent that the lowest parts of the rice stalks are submerged. After 96 hours, the plants are infected with a conidia suspension of the fungus and kept at a relative atmospheric humidity of 95 to 100 per cent and a temperature of 24° C. for 5 days. In most cases, compounds of the formula I prevent the outbreak of disease on the infected plants.

EXAMPLE B-7
Residual-protective Activity Against *Venturia inaequalis* in Apples Apple cuttings with fresh shoots 10 to 20 cm in length are sprayed to drip point with a spray mixture (0.02% active ingredient) and, 24 hours later, infected with a conidia suspension of the fungus. The plants are incubated for 5 days at a relative atmospheric humidity of 90 to 100 per cent and placed in a greenhouse at 20 to 24° for a further 10 days. Scab attack is assessed 15 days after infection. The majority of the compounds of the formula I of one of Tables 1, 2, 3 or 4 have a long-term activity against scab diseases.

EXAMPLE B-8
Activity Against *Erysiphe graminis* in Barley
a) Residual-protective Activity Barley plants about 8 cm in height are sprayed to drip point with an aqueous spray mixture (0.02% of active ingredient) and, 3 to 4 hours later, dusted with conidia of the fungus. The infected plants are placed in a greenhouse at 22°. The fungus infestation is assessed 10 days after infection.

b) Systemic Activity

An aqueous spray mixture (0.002% of active ingredient based on the volume of soil) is poured in the vicinity of barley plants approximately 8 cm in height. Care is taken that the spray mixture does not come into contact with aerial parts of the plants. 48 hours later, the plants are dusted with conidia of the fungus. The infected plants are placed in a greenhouse at 22°. The fungus infestation is assessed 10 days after infection. In general, compounds of the formula I are capable of reducing the disease infestation to less than 20%. Compounds of H-1, H-2, H-4 as well as compounds Nos. 1.13; 1.14; 1.24; 1.86; 1.112; 1.116; 1.117; 1.160; 1.320–1.332; 2.10; 2.12; 2.13; 2.57; 2.101; 2.114–2.124; 3.11; 3.101–3.110; 4.10–4.12; 4.51; 4.93 exhibit almost complete control (0–5% infestation).

EXAMPLE B-9
Activity Against *Podosphaera leucotricha* on Apple Shoots
Residual-protective Activity Apple cuttings which have fresh shoots approximately 15 cm in length are sprayed with a spray mixture (0.06% of active ingredient). After 24 hours, the treated plants are infected with a conidia suspension of the fungus and placed in a controlled-environment cabinet at a relative atmospheric humidity of 70% and at 20° C. The fungus infestation is assessed 12 days after infection.

After treatment with active ingredients of the formula I, the disease infestation is less than 20%. 100% of the control plants are infested. After treatment with compounds of examples H-1, H-2, H-4; Nos. 2.101; 2.115 or 4.51 the fungus attack was almost nil (0–5%).

EXAMPLE B-10
Activity Against *Botrytis Cinerea* on Apple Fruits. Residual-protective Activity Artificially damaged apples are treated by dropwise application to the damaged sites of a spray mixture (0.02% of active ingredient). The treated fruits are subsequently inoculated with a spore suspension of the fungus and incubated for one week at a high humidity and at about 20° C. The fungicidal activity of the test substance is derived from the number and size of the rotted damaged sites.

Active ingredients of the formula I from Table 1, 2, 3 or 4 are capable of preventing the spread of rot. Compounds Nos. 2.10; 2.57; 2.101; 2.115; 2.119–2.122; 3.11; 3.101; 3.102; 3.104–3.109; 4.10; 4.11; 4.51; 4.93 as well as the compounds of examples H-1, H-2 and H-4 display almost complete control (0–5% infestation).

EXAMPLE B-11
Activity Against *Helminthosporium gramineum*

Wheat kernels are contaminated with a spore suspension of the fungus and allowed to dry. The contaminated kernels are dressed with a suspension of the test substance (600 ppm of active ingredient based on the weight of the seeds). After two days, the kernels are placed in suitable agar dishes and, after another four days, the development of fungal colonies around the kernels is assessed. Number and size of the fungal colonies are used to assess the test substance. In some cases, compounds of the formula I exhibit a good activity, i.e. they inhibit the growth of the fungal colonies.

EXAMPLE B-12
Activity Against *Colletotrichum lagenarium* in Cucumbers

Cucumber plants are grown for 2 weeks and then sprayed with a spray mixture (concentration 0.002%). After 2 days, the plants are infected with a spore suspension ($1.5 \times 10^5$ spores/ml) of the fungus and incubated for 36 hours at 23° C. and a high humidity. Incubation is then continued at normal humidity and at about 22–23° C. The fungus infestation which appeared is assessed 8 days after infection. Untreated, but infected control plants exhibit a fungus infestation of 100%. In some cases, compounds of the formula I cause virtually complete inhibition of disease infestation.

EXAMPLE B-13
Activity Against *Fusarium nivale* in Rye

Rye cv. Tetrahell which is naturally infected with Fusarium nivale is treated with the test fungicide in a roller mixer, the following concentrations being used: 20 or 6 ppm of AI (based on the weight of the seeds).

The infected and treated rye is sown in October in the open field in plots of 3 m length and 6 seed rows, using a seed drill. 3 replications per concentration.

Until the infestation is completely evaluated, the test plants are grown under normal field conditions (preferably in a region where there is a closed covering of snow over the winter months).

To assess the phytotoxicity, seed emergence is rated in autumn and plant density/pillaring is rated in spring.

To determine the activity of the active ingredient, the percentage of Fusarium-infested plants is counted in spring immediately after the snow has melted. In the present case, the number of infested plants was less than 5%. The appearance of the emerged plants was healthy.

EXAMPLE B-14
Activity Against *Septoria nodorum* in Wheat

Wheat plants at the 3-leaf stage are sprayed with a spray mixture (60 ppm of active ingredient) prepared with a wettable powder of the active ingredients (2.8:1).

After 24 hours, the treated plants are infected with a conidia suspension of the fungus. The plants are subsequently incubated for 2 days at a relative atmospheric humidity of 90–100% and placed in a greenhouse at 20–24° C. for a further 10 days. 13 days after infection, the fungus infestation is assessed. Less than 1% of the wheat plants were infested.

EXAMPLE B-15
Activity Against *Rhizoctonia solani* on Rice
Protective Local Soil Drench A suspension (spray mixture) prepared with a formulated test substance is poured in the vicinity of 10-day-old rice plants without contaminating aerial parts of the plants. Three days later, the plants are infected by placing a piece of barley straw which is infected with *Rhizoctonia solani* between the rice plants. After incubation for 6 days in a controlled-environment cabin at a daytime temperature of 29° C. and a night temperature of 26° C. and a relative atmospheric humidity of 95%, the fungus infestation is assessed. Less than 5% of the rice plants are infested. The appearance of the plants is healthy.

Protective Local Foliar Application 12-day-old rice plants are sprayed with a suspension prepared with formulated test substances. One day later, the plants are infected by placing a piece of barley straw which is infected with *Rhizoctonia solani* between the rice plants. After incubation for 6 days in a controlled-environment cabin at a daytime temperature of 29° C. and a night temperature of 26° C. and a relative atmospheric humidity of 95%, the plants are rated. Untreated, but infected control plants display a fungus infestation of 100%. In some cases, compounds of the formula I cause virtually complete inhibition of disease infestation.

What is claimed is:

1. A compound of the formula I or an acid addition salt thereof (I)

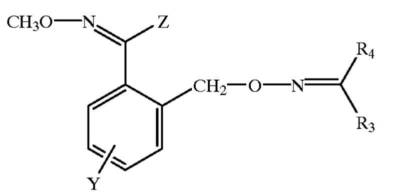

in which

Y is hydrogen, $C_1$–$C_4$alkyl, $C_1$–$C_4$alkoxy, OH, CN, $NO_2$, $Si(CH_3)_3$, $CF_3$ or halogen, Z is a group b)

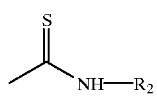

and in which the remaining substituents are defined as follows:

$R_2$ is hydrogen, $C_1$–$C_4$alkyl, $C_2$–$C_4$alkenyl, $C_2$–$C_4$alkynyl, $C_3$–$C_6$cycloalkyl, C(O)$R_6$, OH $C_1$–$C_4$alkoxy, $NH_2$ or $C_1$–$C_4$alkylamine;

$R_6$ is hydrogen, $C_1$–$C_4$alkyl, $C_1$–$C_4$haloalkyl, $C_1$–$C_4$alkoxy, $C_3$–$C_6$cycloalkyl, $C_1$–$C_4$alkoxycarbonyl or phenyl which is unsubstituted or at most trisubstituted;

and in which $R_3$ and $R_4$ independently of one another are hydrogen, cyano, $C_1$–$C_4$alkyl, halo-$C_1$–$C_4$alkyl, $C_2$–$C_4$alkenyl, $C_2$–$C_4$alkynyl, $C_3$–$C_6$cycloalkyl, cyclopropylmethyl, $C_1$–$C_4$alkoxy, $C_2$–$C_5$alkoxyalkyl, $C_1$–$C_4$alkoxycarbonyl, $C_1$–$C_4$alkylthio, $C_2$–$C_5$alkylthioalkyl; a ring having not more than 15 ring carbon atoms which can be polymembered, and is unsubstituted or at most trisubstituted and has 0–3 hetero atoms N, O or S, it being possible for this ring to be bonded via an aliphatic bridge having not more than 4 carbon atoms and/or via either CO, oxygen or sulfur; or in which $R_3$ and $R_4$ together with the shared carbon atom are a ring or a polymembered ring system having not more than 15 ring carbon atoms which is unsubstituted or at most trisubstituted and has 0–3 hetero atoms N, O or S;

the possible substituents of all these rings mentioned for $R_3$ and $R_4$, either individually or in combination, being selected from amongst $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, NH($C_1$–$C_4$alkyl), N($C_1$–$C_4$alkyl)$_2$, $C_1$–$C_4$alkoxymethyl, $C_1$–$C_4$alkylcarbonyl, $C_1$–$C_4$alkoxycarbonyl, $C_1$–$C_4$alkoximinomethyl, —$CSNH_2$, —SH, $C_1$–$C_4$alkylthio, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl; phenyl, benzyl, phenoxy, phenylthio, benzyloxy and benzylthio; it being possible for the last-mentioned aromatic substituents to have not more than three further substituents in the phenyl ring which are selected from amongst halogen, $C_1$–$C_4$alkyl, $C_1$–$C_4$alkoxy, $C_1$–$C_4$haloalkyl, $C_1$–$C_4$haloalkoxy, CN and $NO_2$ and it being possible for two of the substituents, of which there are not more than 3, to form, together with the adjacent substituents, an aliphatic bridge which has not more than 5 members and which has 0–2 oxygen atoms and 0–1 carbonyl group and which can be not more than tetrasubstituted by halogen, $C_1$–$C_4$alkyl, $C_1$–$C_4$alkoxy and/or by a single phenyl group.

2. A compound according to claim 1, wherein $R_2$ is hydrogen, $C_1$–$C_4$alkyl, $C_2$–$C_4$alkenyl, $C_2$–$C_4$alkynyl, $C_3$–$C_6$cycloalkyl, C(O)$R_6$, OH or $C_1$–$C_4$alkoxy.

3. A compound according to claim 1, in which the substituents are defined as follows:

Y is hydrogen,

Z is a group b), $R_2$ is H, $C_1$–$C_4$alkyl, OH, $C_1$–$C_4$alkoxy $R_3$ is H, $C_1$–$C_4$alkyl, cyclopropyl, $C_1$–$C_2$alkoxy, $C_1$–$C_2$alkylthio, methoxymethyl, cyano, trifluoromethyl, $R_4$ is halophenyl having 1 to 2 halogen atoms, mono-$C_1$–$C_2$alkylphenyl, monohalo-mono-($C_1$–$C_2$alkoxy) phenyl, mono-($C_1$–$C_4$-alkoxy)phenyl, 3-(halo-$C_1$–$C_4$alkyl)phenyl having 1 to 3 halogen atoms, trifluoromethylphenyl which is substituted by fluorine or chlorine, 3-(halo-$C_{1-C4}$alkoxy)phenyl having 1 to 6 halogen atoms, 3-($C_2$–$C_4$alkenyloxy)phenyl, 3-($C_2$–$C_4$alkynyloxy)phenyl, 3-($C_3$–$C_6$cycloalkylmethoxy)phenyl, 3-(cyano-$C_1$–$C_3$alkoxy)phenyl, bis(trifluoromethyl)phenyl, tolyl which is substituted by fluorine or chlorine, monocyanophenyl, trifluoromethylphenyl which is substituted by methylthio, or 3-(trimethylsilyl)phenyl, methoxynitrophenyl, 3- or 4-phenoxyphenyl; 3-(methylsulfinylmethyl)- or 3-(methylsulfonylmethyl) phenyl which are unsubstituted or substituted by methoxy; or 3-trifluoromethyl, 4-chlorobenzyl, 3-(trifluoromethyl)phenoxymethyl, 3-trifluoromethylbenzoyl, 2-naphthyl, phenyl which is substituted in the 3- and 4-position by straight-chain $C_1$–$C_3$alkylenedioxy, dihydrobenzofur-5-yl, 2-thienyl, benzofur-2-yl, 2-furyl, 5-chloro- or 5-bromothien-2-yl, 3-methylbenzo[b]thien-2-yl, 1-methylpyrrol-2yl, 2-thiazolyl, 2-pyridyl which is unsubstituted or substituted by halogen or trifluoromethyl, or 6- or 7-quinoxalinyl, 6-quinoxalinyl, 2-pyrimidinyl which is mono- to disubstituted by halogen, methyl, trifluoromethyl, cyclopropyl, $C_1$–$C_3$alkoxy or methylthio; 4-(2,6-dimethylmorpholinyl);

or $R_3$ and $R_4$ together are a 5,6-dihydro-2H-1,4-thiazine ring which is substituted in the 3-position by substituted phenyl, or $R_3$ and $R_4$ together are a cyclopentane or tetrahydropyran ring to which an unsubstituted or halogen-substituted benzene ring is fused.

4. A compound according to claim 1, in which $R_4$ is 3-(halo-$C_1$–$C_4$alkoxy)phenyl having 1 to 6 fluorine atoms.

5. A compound according to claim 1, in which $R_4$ is phenyl which is substituted in the 3- and 4-position by a straight-chain $C_1$–$C_3$alkylenedioxy selected from the group consisting of methylenedioxy, ethylenedioxy, 2,2-difluoromethylenedioxy, and 2-methoxymethylenedioxy.

6. A compound according to claim 3, in which the substituents are defined as follows:

$R_2$ is H, $C_1$–$C_2$alkyl, OH, $C_1$–$C_4$alkoxy $R_3$ is H, $C_1$–$C_2$alkyl, cyclopropyl, methoxy, methylthio, methoxymethyl, cyano, trifluoromethyl, $R_4$ is monohalophenyl, dihalophenyl, mono-$C_1$–$C_2$alkylphenyl, mono-$C_1$–$C_2$alkoxyphenyl, 2-naphthyl, 3,4-methylenedioxyphenyl, 3,4-ethylenedioxyphenyl, 2,2-difluoro-5-benzodioxolyl, 2-methoxy-5-benzodioxolyl, 3-(fluoro-$C_1$–$C_2$alkoxy) phenyl having 1–3 fluorine atoms, 3-trifluoromethylphenyl, 3,5-bis(trifluoromethyl)phenyl, 4-fluoro-3-trifluoromethylphenyl, 3-fluoro-5-trifluoromethylphenyl, 4-chloro-3-trifluoromethylphenyl, 4-chloro-3-tolyl, monocyanophenyl, 3-cyanomethoxyphenyl, 2-methylthio-5'-trifluoromethylphenyl, 4-methoxy-3-nitrophenyl, 3- or 4-phenoxyphenyl, 3-methylsulfinylmethyl-4-methoxyphenyl, 3-methylsulfonyl-4-methoxyphenyl, 3-(prop-1-en-3-yloxy)phenyl, 3-(prop-1-yn-3-yloxy)phenyl, 3-(cyclopropylmethoxy)phenyl, 2,3-dihydrobenzofur-5-yl, 3-trifluoromethyl, 4-chlorobenzyl, 3-trifluoromethylphenoxymethyl, 2-pyridyl, 6-bromo-2-pyridyl, 4-trifluoromethyl-2-pyridyl, 6- or 7-quinolinyl, quinoxalinyl, 2-thienyl, 5-chloro- or bromothien-2-yl, 3-methylbenzo[b]thien-2-yl, 2-furyl, benzo[b]fur-2-yl, 1-methylpyrrol-2-yl, 2-thiazolyl, 4-(2,6-dimethylmorpholinyl); or $R_3$ and $R_4$ together are a 5,6-dihydro-2H-1,4-thiazine ring which is substituted in the 3-position by mono- or dihalophenyl, methoxyphenyl, trifluoromethylphenyl, phenoxy or 3,4-methylenedioxyphenyl, or $R_3$ and $R_4$ together are a cyclopentane or tetrahydropyran ring to which an unsubstituted or fluorine-substituted benzene ring is fused.

7. A compound according to claim 6, wherein $R_2$ is H, methyl, $R_3$ is methyl, methoxy, ethyl, methylthio, cyclopropyl, $R_4$ is 3-halophenyl, 4halophenyl, 3-trifluoromethylphenyl, 3-($C_1$–$C_4$haloethoxy)phenyl, 4fluoro-3-trifluoromethylphenyl, 4tolyl, 3,4-methylenedioxyphenyl, or 3,4-ethylenedioxyphenyl.

8. A compound according to claim 3, wherein $R_2$ is hydrogen, $C_1$–$C_2$alkyl, OH, $C_1$–$C_4$alkoxy, $R_3$ is hydrogen, $C_1$–$C_2$alkyl, cyclopropyl, methoxy, methylthio, methoxymethyl, cyano, trifluoromethyl and $R_4$ is monohalo-monomethoxyphenyl.

9. A compound according to claim 8, wherein $R_4$ is 3-halo-4-methoxyphenyl.

10. A compound according to claim 8, wherein $R_2$ is hydrogen or methyl, $R_3$ is methyl, methoxy, ethyl, methylthio, cyclopropyl; and $R_4$ is 3-halo-4-methoxyphenyl.

11. A pesticidal composition comprising, as active ingredient, a compound of the formula I according to claim 1 together with a suitable carrier material.

12. A process for the preparation of a composition according to claim 11 by intimately mixing and/or grinding the active ingredient with an extender, with or without a surface-active auxiliary.

13. A method of controlling plant diseases and of preventing attack by microorganisms which comprises applying a compound of the formula I according to claim 1 to the plants, parts thereof or to the locus where they grow.

14. A method according to claim 13, wherein the parts of plants are the propagation material.

15. A method according to claim 14, wherein the propagation material is the seeds.

* * * * *